(12) United States Patent
Nishina et al.

(10) Patent No.: US 8,481,938 B2
(45) Date of Patent: Jul. 9, 2013

(54) ELECTROMAGNETIC WAVE MEASURING APPARATUS, MEASURING METHOD, PROGRAM, AND RECORDING MEDIUM

(75) Inventors: Shigeki Nishina, Miyagi (JP); Motoki Imamura, Miyagi (JP); Akiyoshi Irisawa, Miyagi (JP); Tomoyu Yamashita, Miyagi (JP); Eiji Kato, Miyagi (JP)

(73) Assignee: Advantest Corporation, Tokyo (JP)

( * ) Notice: Subject to any disclaimer, the term of this patent is extended or adjusted under 35 U.S.C. 154(b) by 590 days.

(21) Appl. No.: 12/731,617

(22) Filed: Mar. 25, 2010

(65) Prior Publication Data

US 2011/0001048 A1   Jan. 6, 2011

(30) Foreign Application Priority Data

Jul. 1, 2009   (JP) ................................. 2009-157146

(51) Int. Cl.
*G01J 3/00*   (2006.01)
*G01J 9/00*   (2006.01)

(52) U.S. Cl.
USPC ...................................... 250/336.1; 382/131

(58) Field of Classification Search
USPC ...................................... 250/336.1; 382/131
See application file for complete search history.

(56) References Cited

U.S. PATENT DOCUMENTS

| | | | |
|---|---|---|---|
| 6,687,010 B1 | 2/2004 | Horii et al. | |
| 6,873,405 B2 * | 3/2005 | Kido et al. | 356/121 |
| 7,119,339 B2 | 10/2006 | Ferguson et al. | |
| 8,183,528 B2 * | 5/2012 | Kato et al. | 250/358.1 |
| 2004/0109164 A1 | 6/2004 | Horii et al. | |
| 2005/0227660 A1 * | 10/2005 | Hashemi et al. | 455/276.1 |
| 2007/0222693 A1 * | 9/2007 | Popa-Simil | 343/753 |
| 2008/0116374 A1 | 5/2008 | Ouchi et al. | |
| 2010/0271001 A1 * | 10/2010 | Kato et al. | 324/76.12 |
| 2010/0271056 A1 * | 10/2010 | Irisawa et al. | 324/750 |
| 2010/0295534 A1 * | 11/2010 | Nishina et al. | 324/76.39 |
| 2010/0321682 A1 * | 12/2010 | Kato et al. | 356/244 |
| 2011/0057103 A1 * | 3/2011 | Nishina et al. | 250/338.1 |
| 2011/0075127 A1 * | 3/2011 | Nishina et al. | 356/51 |
| 2011/0094300 A1 * | 4/2011 | Imamura et al. | 73/32 A |
| 2011/0097649 A1 * | 4/2011 | Imamura et al. | 429/523 |
| 2011/0108740 A1 * | 5/2011 | Naitoh | 250/491.1 |

FOREIGN PATENT DOCUMENTS

| | | |
|---|---|---|
| JP | 8-304229 | 11/1996 |
| JP | 2001-021448 | 1/2001 |
| JP | 2001-264246 | 9/2001 |
| JP | 2008-116439 | 5/2008 |

OTHER PUBLICATIONS

Wang, S and X.C. Zhang, "Pulse Tetahertz Tomography," J. Phys. D: Appl. Phys. 37 (2004) R1-R36.*

(Continued)

*Primary Examiner* — Casey Bryant
(74) *Attorney, Agent, or Firm* — Greenblum & Bernstein, P.L.C.

(57) ABSTRACT

According to the present invention, an electromagnetic wave measurement device includes an electromagnetic wave output device, an electromagnetic wave detector, a relative position changing unit, a delay period recording unit, a phase deriving unit, a delay-corrected phase deriving unit, a sinogram deriving unit, and an image deriving unit. The electromagnetic wave output device outputs an electromagnetic wave having a frequency equal to or more than 0.01 THz and equal to or less than 100 THz toward a device under test and a container storing at least a part of the device under test.

12 Claims, 15 Drawing Sheets

OTHER PUBLICATIONS

Ferguson et al., "T-ray computed tomography," Optics Letters, vol. 27, No. 15, pp. 1312-1314, Aug. 1, 2002.

Ferguson et al., "Towards functional 3D T-ray imaging," Physics in Medicine and Biology, vol. 47, No. 21, pp. 3735-3742, Oct. 17, 2002.

S. Wang et al., "Pulsed terahertz tomography," J. Phys. D: Appl. Phys., vol. 37, pp. R1-R36, Jan. 28, 2004.

U.S. Appl. No. 12/487,177 to Kato et al., filed Jun. 18, 2009.

U.S. Appl. No. 12/731,483 to Nishina et al., filed Mar. 25, 2010.

* cited by examiner

ELECTROMAGNETIC WAVE MEASURING APPARATUS, MEASURING METHOD, PROGRAM, AND RECORDING MEDIUM

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been the computed tomography (CT) as a method for obtaining tomographic information on a device under test. This method conducted while a generator and a detector of the X ray are used is referred to as X-ray CT. With the X-ray CT, it is possible to acquire tomographic information on a human body in non-destructive and non-contact manner.

However, it is difficult for the X-ray CT to detect internal states (such as defects and distortions) of industrial products constructed by semiconductors, plastics, ceramics, woods, and papers (referred to as "raw materials" hereinafter). This is because the X-ray presents a high transmission property to any materials.

On the other hand, the terahertz wave properly transmits through the raw materials of the industrial products described above. Therefore, the CT carried out while a generator and a detector of the terahertz wave are used (referred to as "terahertz CT" hereinafter) can detect internal states of the industrial products. Patent Document 1 and Non-Patent Document 1 describe the terahertz CT.

(Patent Document 1) U.S. Pat. No. 7,119,339
(Non-Patent Document 1) S. Wang et al., "Pulsed terahertz tomography," J. Phys. D, Vol. 37 (2004), R1-R36

SUMMARY OF THE INVENTION

However, in the terahertz CT, due to a refractive index of the device under test and a refractive index of a surrounding of the device under test, an error may be generated after the detection of the terahertz wave.

Therefore, it is an object of the present invention, when an electromagnetic wave (frequency thereof is equal to or more than 0.01 [THz] and equal to or less than 100 [THz]) including the terahertz wave is fed to a device under test (DUT) for measurement, to remove an error of a value of the detected electromagnetic wave including the terahertz wave.

According to the present invention, an electromagnetic wave measurement device includes: an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a delay period recording unit that records a delay period of the electromagnetic wave caused by a transmission of the electromagnetic wave through the container; a phase deriving unit that derives, based on a detected result by the electromagnetic wave detector, a phase in the frequency domain of the electromagnetic wave which has transmitted through the device under test; a delay-corrected phase deriving unit that derives a delay-corrected phase obtained by subtracting an integral of the delay period with respect to the frequency from the phase; a sinogram deriving unit that derives a sinogram based on a derived result by the delay-corrected phase deriving unit; and an image deriving unit that derives, based on the sinogram, an image of a cross section of the device under test including the intersection.

According to the present invention, the electromagnetic wave measurement device may include a group delay deriving unit that derives, based on the derived result by the delay-corrected phase deriving unit, a group delay in the frequency domain of the electromagnetic wave which has transmitted through the device under test, wherein the sinogram deriving unit derives a sinogram for the group delay.

According to the present invention, the electromagnetic wave measurement device may include a chromatic dispersion deriving unit that derives, based on the derived result by the delay-corrected phase deriving unit, a chromatic dispersion in the frequency domain of the electromagnetic wave which has transmitted through the device under test, wherein the sinogram deriving unit derives a sinogram for the chromatic dispersion.

According to the present invention, an electromagnetic wave measurement device includes: an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; a relative position changing unit that changes a relative position of a first intersection at which an optical path of the electromagnetic wave transmitting through the first device under test and the first device under test intersect with respect to the first device under test; a delay period recording unit that records a delay period of the electromagnetic wave caused by a transmission of the electromagnetic wave through the container; a phase deriving unit that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving unit that derives a delay-corrected phase obtained by subtracting an integral of the delay period with respect to the frequency from the first phase; a group delay deriving unit that derives, based on a derived result by the delay-corrected phase deriving unit and the second phase, a first group delay in the frequency domain of the electromagnetic wave which has transmitted through the first device under test, and a second group delay in the frequency domain of the electromagnetic wave which has transmitted through the second device under test; a sinogram deriving unit that derives, based on a difference between the first group delay and the second group delay, a sinogram for a difference in the group delay between the first device under test and the second device under test; and an image deriving unit that derives, based on the sinogram, an image of a cross section of the device under test including the intersection.

According to the electromagnetic wave measurement device of the present invention, the refractive index of the second device under test may be known; and the sinogram deriving unit may derive a sinogram for the refractive index of the first device under test based on the difference between the first group delay and the second group delay.

According to the present invention, an electromagnetic wave measurement device includes: an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; a relative position changing unit that changes a relative position of a first intersection at which an optical path of the electromagnetic wave transmitting through the first device under test and the first device under test intersect with respect to the first device under test; a delay period recording unit that records a delay period of the electromagnetic wave caused by a transmission of the electromagnetic wave through the container; a phase deriving unit that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving unit that derives a delay-corrected phase obtained by subtracting an integral of the delay period with respect to the frequency from the first phase; a group delay deriving unit that derives, based on a derived result by the delay-corrected phase deriving unit and the second phase, a first group delay in the frequency domain of the electromagnetic wave which has transmitted through the first device under test, and a second group delay in the frequency domain of the electromagnetic wave which has transmitted through the second device under test; a sinogram deriving unit that derives a first sinogram based on the first group delay, and a second sinogram based on the second group delay; and an image deriving unit that derives an image of a cross section of the first device under test based on the first sinogram, and an image of a cross section of the second device under test based on the second sinogram, and, as a difference between the image of the cross section of the first device under test and the image of the cross section of the second device under test, derives an image representing a difference in the group delay between the first device under test and the second device under test.

According to the present invention, an electromagnetic wave measurement device includes: an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a phase deriving unit that derives, based on a detected result by the electromagnetic wave detector, a phase in the frequency domain of the electromagnetic wave which has transmitted through the device under test; a group delay deriving unit that derives, based on a derived result by the phase deriving unit, a group delay in the frequency domain of the electromagnetic wave which has transmitted through the device under test; a sinogram deriving unit that derives a sinogram based on a derived result by the group delay deriving unit; a delay period recording unit that records a delay period of the electromagnetic wave caused by a transmission of the electromagnetic wave through the container; a delay-corrected sinogram deriving unit that derives a delay-corrected sinogram obtained by subtracting the delay period from the sinogram; and an image deriving unit that derives, based on the delay-corrected sinogram, an image of a cross section of the device under test including the intersection.

According to the present invention, an electromagnetic wave measurement device includes: an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; a relative position changing unit that changes a relative position of a first intersection at which an optical path of the electromagnetic wave transmitting through the first device under test and the first device under test intersect with respect to the first device under test; a phase deriving unit that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving unit that derives, based on a derived result by the phase deriving unit, a first group delay in the frequency domain of the electromagnetic wave which has transmitted through the first device under test, and a second group delay in the frequency domain of the electromagnetic wave which has transmitted through the second device under test; a sinogram deriving unit that derives, based on a difference between the first group delay and the second group delay, a sinogram for a difference in the group delay between the first device under test and the second device under test; a delay period recording unit that records a delay period of the electromagnetic wave caused by a transmission of the electromagnetic wave through the container; a delay-corrected sinogram deriving unit that derives a delay-corrected sinogram obtained by subtracting the delay period from the sinogram; and an image deriving unit that derives, based on the delay-corrected sinogram, an image of a cross section of the device under test including the intersection.

According to the electromagnetic wave measurement device of the present invention, the refractive index of the second device under test may be known; and the sinogram deriving unit may derive a sinogram for the refractive index of the first device under test based on the difference between the first group delay and the second group delay.

According to the present invention, an electromagnetic wave measurement device includes: an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; a relative position changing unit that changes a relative position of a first intersection at which an optical path of the electromagnetic wave transmitting through the first device under test and the first device under test intersect with respect to the first device under test; a phase deriving unit that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving unit that derives, based on a derived result by the phase deriving unit, a first group delay in the frequency domain of the electromagnetic wave which has transmitted through the first device under test, and a second group delay in the frequency domain of the electromagnetic wave which has transmitted through the second device under test; a sinogram deriving unit that derives a first sinogram based on the first group delay, and a second sinogram based on the second group delay; a delay period recording unit that records a delay period of the electromagnetic wave caused by a transmission of the electromagnetic wave through the container; a delay-corrected sinogram deriving unit that derives a delay-corrected sinogram obtained by subtracting the delay period from the first sinogram; and an image deriving unit that derives an image of a cross section of the first device under test based on the delay-corrected sinogram, and an image of a cross section of the second device under test based on the second sinogram, and, as a difference between the image of the cross section of the first device under test and the image of the cross section of second device under test, derives an image representing a difference in the group delay between the first device under test and the second device under test.

According to the present invention, an electromagnetic wave measurement device includes: an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a phase deriving unit that derives, based on a detected result by the electromagnetic wave detector, a phase in the frequency domain of the electromagnetic wave which has transmitted through the device under test; a chromatic dispersion deriving unit that derives, based on a derived result by the phase deriving unit, a chromatic dispersion in the frequency domain of the electromagnetic wave which has transmitted through the device under test; a sinogram deriving unit that derives a sinogram based on a derived result by the chromatic dispersion deriving unit; a delay period recording unit that records a delay period of the electromagnetic wave caused by a transmission of the electromagnetic wave through the container; a delay-corrected sinogram deriving unit that derives a delay-corrected sinogram obtained by subtracting a value, which is obtained by partially differentiating the group delay with respect to the frequency, from the sinogram; and an image deriving unit that derives, based on the delay-corrected sinogram, an image of a cross section of the device under test including the intersection.

According to the present invention, an electromagnetic wave measurement device includes: an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a transmittance recording unit that records a value representing a transmittance of a power of the electromagnetic wave transmitting through the container while a reflection of the electromagnetic wave on a transmission surface through which the electromagnetic wave transmits in the container is considered; a corrected power deriving unit that derives a corrected power which is a power of the electromagnetic wave detected when the transmittance is 100% based on a power of the electromagnetic wave detected by the electromagnetic wave detector and the transmittance; an attenuation ratio deriving unit that derives an attenuation ratio of the electromagnetic wave which has transmitted through the device under test based on the corrected power; and an inverse radon transform unit that applies the inverse radon transform to a derived result by the attenuation ratio deriving unit.

According to the present invention, an electromagnetic wave measurement device includes: an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a phase deriving unit that derives, based on a detected result by the electromagnetic wave detector, a phase in the frequency domain of the electromagnetic wave which has transmitted through the device under test; a group delay deriving unit that derives, based on a derived result by the phase deriving unit, a group delay in the frequency domain of the electromagnetic wave which has transmitted through the device under test; a delay period recording unit that records a delay period of the electromagnetic wave caused by a transmission of the electromagnetic wave through the container; a group delay correction unit that derives a corrected group delay obtained by subtracting the delay period from the group delay; a sinogram deriving unit that derives a sinogram based on the corrected group delay; and an image deriving unit that derives, based on the sinogram, an image of a cross section of the device under test including the intersection.

According to the present invention, an electromagnetic wave measurement device includes: an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; a relative position changing unit that changes a relative position of a first intersection at which an optical path of the electromagnetic wave transmitting through the first device under test and the first device under test intersect with respect to the first device under test; a phase deriving unit that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving unit that derives, based on a derived result by the phase deriving unit, a first group delay in the frequency domain of the electromagnetic wave which has transmitted through the first device under test, and a second group delay in the frequency domain of the electromagnetic wave which has transmitted through the second device under test; a delay period recording unit that records a delay period of the electromagnetic wave caused by a transmission of the electromagnetic wave through the container; a group delay correction unit that derives a corrected group delay obtained by subtracting the delay period from the first group delay; a sinogram deriving unit that derives, based on a difference between the corrected group delay and the second group delay, a sinogram for a difference in the group delay between the first device under test and the second device under test; and an image deriving unit that derives, based on the sinogram, an image of a cross section of the device under test including the intersection.

According to the electromagnetic wave measurement device of the present invention, the refractive index of the second device under test may be known; and the sinogram deriving unit may derive a sinogram for the refractive index of the first device under test based on the difference between the corrected group delay and the second group delay.

According to the present invention, an electromagnetic wave measurement device includes: an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; a relative position changing unit that changes a relative position of an intersection at which an optical path of the electromagnetic wave transmitting through the device under test and the device under test intersect with respect to the device under test; a phase deriving unit that derives, based on a detected result by the electromagnetic wave detector, a phase in the frequency domain of the electromagnetic wave which has transmitted through the device under test; a chromatic dispersion deriving unit that derives, based on a derived result by the phase deriving unit, a chromatic dispersion in the frequency domain of the electromagnetic wave which has transmitted through the device under test; a delay period recording unit that records a delay period of the electromagnetic wave caused by a transmission of the electromagnetic wave through the container; a chromatic dispersion correction unit that derives a corrected chromatic dispersion obtained by subtracting a value, which is obtained by partially differentiating the group delay with respect to the frequency, from the chromatic dispersion; a sinogram deriving unit that derives a sinogram based on the corrected chromatic dispersion; and an image deriving unit that derives, based on the sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the method including: a delay period recording step that records a delay period of the electromagnetic wave caused by a transmission of the electromagnetic wave through the container; a phase deriving step that derives, based on a detected result by the electromagnetic wave detector, a phase in the frequency domain of the electromagnetic wave which has transmitted through the device under test; a delay-corrected phase deriving step that derives a delay-corrected phase obtained by subtracting an integral of the delay period with respect to the frequency from the phase; a sinogram deriving step that derives a sinogram based on a derived result by the delay-corrected phase deriving step; and an image deriving step that derives, based on the sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the method including: a delay period recording step that records a delay period of the electromagnetic wave caused by a transmission of the electromagnetic wave through the container; a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving step that derives a delay-corrected phase obtained by subtracting an integral of the delay period with respect to the frequency from the first phase; a group delay deriving step that derives, based on a derived result by the delay-corrected phase deriving step and the second phase, a first group delay in the frequency domain of the electromagnetic wave which has transmitted through the first device under test, and a second group delay in the frequency domain of the electromagnetic wave which has transmitted through the second device under test; a sinogram deriving step that derives, based on a difference between the first group delay and the second group delay, a sinogram for a difference in the group delay between the first device under test and the second device under test; and an image deriving step that derives, based on the sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the method including: a delay period recording step that records a delay period of the electromagnetic wave caused by a transmission of the electromagnetic wave through the container; a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving step that derives a delay-corrected phase obtained by subtracting an integral of the delay period with respect to the frequency from the first phase; a group delay deriving step that derives, based on a derived result by the delay-corrected phase deriving step and the second phase, a first group delay in the frequency domain of the electromagnetic wave which has transmitted through the first device under test, and a second group delay in the frequency domain of the electromagnetic wave which has transmitted through the second device under test; a sinogram deriving step that derives a first sinogram based on the first group delay, and a second sinogram based on the second group delay; and an image deriving step that derives an image of a cross section of the first device under test based on the first sinogram, and an image of a cross section of the second device under test based on the second sinogram, and, as a difference between the image of the cross section of the first device under test and the image of the cross section of the second device under test, derives an image representing a difference in the group delay between the first device under test and the second device under test.

The present invention is a measurement method using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the method including: a phase deriving step that derives, based on a detected result by the electromagnetic wave detector, a phase in the frequency domain of the electromagnetic wave which has transmitted through the device under test; a group delay deriving step that derives, based on a derived result by the phase deriving step, a group delay in the frequency domain of the electromagnetic wave which has transmitted through the device under test; a sinogram deriving step that derives a sinogram based on a derived result by the group delay deriving step; a delay period recording step that records a delay period of the electromagnetic wave caused by a transmission of the electromagnetic wave through the container; a delay-corrected sinogram deriving step that derives a delay-corrected sinogram obtained by subtracting the delay period from the sinogram; and an image deriving step that derives, based on the delay-corrected sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the method including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a sinogram deriving step that derives, based on a difference between the first group delay and the second group delay, a sinogram for a difference in the group delay between the first device under test and the second device under test; a delay period recording step that records a delay period of the electromagnetic wave caused by a transmission of the electromagnetic wave through the container; a delay-corrected sinogram deriving step that derives a delay-corrected sinogram obtained by subtracting the delay period from the sinogram; and an image deriving step that derives, based on the delay-corrected sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the method including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a sinogram deriving step that derives a first sinogram based on the first group delay, and a second sinogram based on the second group delay; a delay period recording step that records a delay period of the electromagnetic wave caused by a transmission of the electromagnetic wave through the container; a delay-corrected sinogram deriving step that derives a delay-corrected sinogram obtained by subtracting the delay period from the first sinogram; and an image deriving step that derives an image of a cross section of the first device under test based on the delay-corrected sinogram, and an image of a cross section of the second device under test based on the second sinogram, and, as a difference between the image of the cross section of the first device under test and the image of the cross section of second device under test, derives an image representing a difference in the group delay between the first device under test and the second device under test.

The present invention is a measurement method using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the method including: a phase deriving step that derives, based on a detected result by the electromagnetic wave detector, a phase in the frequency domain of the electromagnetic wave which has transmitted through the device under test; a chromatic dispersion deriving step that derives, based on a derived result by the phase deriving step, a chromatic dispersion in the frequency domain of the electromagnetic wave which has transmitted through the device under test; a sinogram deriving step that derives a sinogram based on a derived result by the chromatic dispersion deriving step; a delay period recording step that records a delay period of the electromagnetic wave caused by a transmission of the electromagnetic wave through the container; a delay-corrected sinogram deriving step that derives a delay-corrected sinogram obtained by subtracting a value, which is obtained by partially differentiating the group delay with respect to the frequency, from the sinogram; and an image deriving step that derives, based on the delay-corrected sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the method including: a transmittance recording step that records a value representing a transmittance of a power of the electromagnetic wave transmitting through the container while a reflection of the electromagnetic wave on a transmission surface through which the electromagnetic wave transmits in the container is considered; a corrected power deriving step that derives a corrected power which is a power of the electromagnetic wave detected when the transmittance is 100% based on a power of the electromagnetic wave detected by the electromagnetic wave detector and the transmittance; an attenuation ratio deriving step that derives an attenuation ratio of the electromagnetic wave which has transmitted through the device under test based on the corrected power; and an inverse radon transform step that applies the inverse radon transform to a derived result by the attenuation ratio deriving step.

The present invention is a measurement method using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the method including: a phase deriving step that derives, based on a detected result by the electromagnetic wave detector, a phase in the frequency domain of the electromagnetic wave which has transmitted through the device under test; a group delay deriving step that derives, based on a derived result by the phase deriving step, a group delay in the frequency domain of the electromagnetic wave which has transmitted through the device under test; a delay period recording step that records a delay period of the electromagnetic wave caused by a transmission of the electromagnetic wave through the container; a group delay correction step that derives a corrected group delay obtained by subtracting the delay period from the group delay; a sinogram deriving step that derives a sinogram based on the corrected group delay; and an image deriving step that derives, based on the sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the method includes: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a delay period recording step that records a delay period of the electromagnetic wave caused by a transmission of the electromagnetic wave through the container; a group delay correction step that derives a corrected group delay obtained by subtracting the delay period from the first group delay; a sinogram deriving step that derives, based on a difference between the corrected group delay and the second group delay, a sinogram for a difference in the group delay between the first device under test and the second device under test; and an image deriving step that derives, based on the sinogram, an image of a cross section of the device under test including the intersection.

The present invention is a measurement method using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the method including: a phase deriving step that derives, based on a detected result by the electromagnetic wave detector, a phase in the frequency domain of the electromagnetic wave which has transmitted through the device under test; a chromatic dispersion deriving step that derives, based on a derived result by the phase deriving step, a chromatic dispersion in the frequency domain of the electromagnetic wave which has transmitted through the device under test; a delay period recording step that records a delay period of the electromagnetic wave caused by a transmission of the electromagnetic wave through the container; a chromatic dispersion correction step that derives a corrected chromatic dispersion obtained by subtracting a value, which is obtained by partially differentiating the group delay with respect to the frequency, from the chromatic dispersion; a sinogram deriving step that derives a sinogram based on the corrected chromatic dispersion; and an image deriving step that derives, based on the sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a delay period recording step that records a delay period of the electromagnetic wave caused by a transmission of the electromagnetic wave through the container; a phase deriving step that derives, based on a detected result by the electromagnetic wave detector, a phase in the frequency domain of the electromagnetic wave which has transmitted through the device under test; a delay-corrected phase deriving step that derives a delay-corrected phase obtained by subtracting an integral of the delay period with respect to the frequency from the phase; a sinogram deriving step that derives a sinogram based on a derived result by the delay-corrected phase deriving step; and an image deriving step that derives, based on the sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a delay period recording step that records a delay period of the electromagnetic wave caused by a transmission of the electromagnetic wave through the container; a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving step that derives a delay-corrected phase obtained by subtracting an integral of the delay period with respect to the frequency from the first phase; a group delay deriving step that derives, based on a derived result by the delay-corrected phase deriving step and the second phase, a first group delay in the frequency domain of the electromagnetic wave which has transmitted through the first device under test, and a second group delay in the frequency domain of the electromagnetic wave which has transmitted through the second device under test; a sinogram deriving step that derives, based on a difference between the first group delay and the second group delay, a sinogram for a difference in the group delay between the first device under test and the second device under test; and an image deriving step that derives, based on the sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a delay period recording step that records a delay period of the electromagnetic wave caused by a transmission of the electromagnetic wave through the container; a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving step that derives a delay-corrected phase obtained by subtracting an integral of the delay period with respect to the frequency from the first phase; a group delay deriving step that derives, based on a derived result by the delay-corrected phase deriving step and the second phase, a first group delay in the frequency domain of the electromagnetic wave which has transmitted through the first device under test, and a second group delay in the frequency domain of the electromagnetic wave which has transmitted through the second device under test; a sinogram deriving step that derives a first sinogram based on the first group delay, and a second sinogram based on the second group delay; and an image deriving step that derives an image of a cross section of the first device under test based on the first sinogram, and an image of a cross section of the second device under test based on the second sinogram, and, as a difference between the image of the cross section of the first device under test and the image of the cross section of the second device under test, derives an image representing a difference in the group delay between the first device under test and the second device under test.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a group delay deriving step that derives, based on a derived result by the phase deriving step, a group delay in the frequency domain of the electromagnetic wave which has transmitted through the device under test; a sinogram deriving step that derives a sinogram based on a derived result by the group delay deriving step; a delay period recording step that records a delay period of the electromagnetic wave caused by a transmission of the electromagnetic wave through the container; a delay-corrected sinogram deriving step that derives a delay-corrected sinogram obtained by subtracting the delay period from the sinogram; and an image deriving step that derives, based on the delay-corrected sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a sinogram deriving step that derives, based on a difference between the first group delay and the second group delay, a sinogram for a difference in the group delay between the first device under test and the second device under test; a delay period recording step that records a delay period of the electromagnetic wave caused by a transmission of the electromagnetic wave through the container; a delay-corrected sinogram deriving step that derives a delay-corrected sinogram obtained by subtracting the delay period from the sinogram; and an image deriving step that derives, based on the delay-corrected sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a sinogram deriving step that derives a first sinogram based on the first group delay, and a second sinogram based on the second group delay; a delay period recording step that records a delay period of the electromagnetic wave caused by a transmission of the electromagnetic wave through the container; a delay-corrected sinogram deriving step that derives a delay-corrected sinogram obtained by subtracting the delay period from the first sinogram; and an image deriving step that derives an image of a cross section of the first device under test based on the delay-corrected sinogram, and an image of a cross section of the second device under test based on the second sinogram, and, as a difference between the image of the cross section of the first device under test and the image of the cross section of second device under test, derives an image representing a difference in the group delay between the first device under test and the second device under test.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a chromatic dispersion deriving step that derives, based on a derived result by the phase deriving step, a chromatic dispersion in the frequency domain of the electromagnetic wave which has transmitted through the device under test; a sinogram deriving step that derives a sinogram based on a derived result by the chromatic dispersion deriving step; a delay period recording step that records a delay period of the electromagnetic wave caused by a transmission of the electromagnetic wave through the container; a delay-corrected sinogram deriving step that derives a delay-corrected sinogram obtained by subtracting a value, which is obtained by partially differentiating the group delay with respect to the frequency, from the sinogram; and an image deriving step that derives, based on the delay-corrected sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a transmittance recording step that records a value representing a transmittance of a power of the electromagnetic wave transmitting through the container while a reflection of the electromagnetic wave on a transmission surface through which the electromagnetic wave transmits in the container is considered; a corrected power deriving step that derives a corrected power which is a power of the electromagnetic wave detected when the transmittance is 100% based on a power of the electromagnetic wave detected by the electromagnetic wave detector and the transmittance; an attenuation ratio deriving step that derives an attenuation ratio of the electromagnetic wave which has transmitted through the device under test based on the corrected power; and an inverse radon transform step that applies the inverse radon transform to a derived result by the attenuation ratio deriving step.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a group delay deriving step that derives, based on a derived result by the phase deriving step, a group delay in the frequency domain of the electromagnetic wave which has transmitted through the device under test; a delay period recording step that records a delay period of the electromagnetic wave caused by a transmission of the electromagnetic wave through the container; a group delay correction step that derives a corrected group delay obtained by subtracting the delay period from the group delay; a sinogram deriving step that derives a sinogram based on the corrected group delay; and an image deriving step that derives, based on the sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a delay period recording step that records a delay period of the electromagnetic wave caused by a transmission of the electromagnetic wave through the container; a group delay correction step that derives a corrected group delay obtained by subtracting the delay period from the first group delay; a sinogram deriving step that derives, based on a difference between the corrected group delay and the second group delay, a sinogram for a difference in the group delay between the first device under test and the second device under test; and an image deriving step that derives, based on the sinogram, an image of a cross section of the device under test including the intersection.

The present invention is a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a chromatic dispersion deriving step that derives, based on a derived result by the phase deriving step, a chromatic dispersion in the frequency domain of the electromagnetic wave which has transmitted through the device under test; a delay period recording step that records a delay period of the electromagnetic wave caused by a transmission of the electromagnetic wave through the container; a chromatic dispersion correction step that derives a corrected chromatic dispersion obtained by subtracting a value, which is obtained by partially differentiating the group delay with respect to the frequency, from the chromatic dispersion; a sinogram deriving step that derives a sinogram based on the corrected chromatic dispersion; and an image deriving step that derives, based on the sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a delay period recording step that records a delay period of the electromagnetic wave caused by a transmission of the electromagnetic wave through the container; a phase deriving step that derives, based on a detected result by the electromagnetic wave detector, a phase in the frequency domain of the electromagnetic wave which has transmitted through the device under test; a delay-corrected phase deriving step that derives a delay-corrected phase obtained by subtracting an integral of the delay period with respect to the frequency from the phase; a sinogram deriving step that derives a sinogram based on a derived result by the delay-corrected phase deriving step; and an image deriving step that derives, based on the sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a delay period recording step that records a delay period of the electromagnetic wave caused by a transmission of the electromagnetic wave through the container; a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving step that derives a delay-corrected phase obtained by subtracting an integral of the delay period with respect to the frequency from the first phase; a group delay deriving step that derives, based on a derived result by the delay-corrected phase deriving step and the second phase, a first group delay in the frequency domain of the electromagnetic wave which has transmitted through the first device under test, and a second group delay in the frequency domain of the electromagnetic wave which has transmitted through the second device under test; a sinogram deriving step that derives, based on a difference between the first group delay and the second group delay, a sinogram for a difference in the group delay between the first device under test and the second device under test; and an image deriving step that derives, based on the sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a delay period recording step that records a delay period of the electromagnetic wave caused by a transmission of the electromagnetic wave through the container; a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a delay-corrected phase deriving step that derives a delay-corrected phase obtained by subtracting an integral of the delay period with respect to the frequency from the first phase; a group delay deriving step that derives, based on a derived result by the delay-corrected phase deriving step and the second phase, a first group delay in the frequency domain of the electromagnetic wave which has transmitted through the first device under test, and a second group delay in the frequency domain of the electromagnetic wave which has transmitted through the second device under test; a sinogram deriving step that derives a first sinogram based on the first group delay, and a second sinogram based on the second group delay; and an image deriving step that derives an image of a cross section of the first device under test based on the first sinogram, and an image of a cross section of the second device under test based on the second sinogram, and, as a difference between the image of the cross section of the first device under test and the image of the cross section of the second device under test, derives an image representing a difference in the group delay between the first device under test and the second device under test.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including; a phase deriving step that derives, based on a detected result by the electromagnetic wave detector, a phase in the frequency domain of the electromagnetic wave which has transmitted through the device under test; a group delay deriving step that derives, based on a derived result by the phase deriving step, a group delay in the frequency domain of the electromagnetic wave which has transmitted through the device under test; a sinogram deriving step that derives a sinogram based on a derived result by the group delay deriving step; a delay period recording step that records a delay period of the electromagnetic wave caused by a transmission of the electromagnetic wave through the container; a delay-corrected sinogram deriving step that derives a delay-corrected sinogram obtained by subtracting the delay period from the sinogram; and an image deriving step that derives, based on the delay-corrected sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a sinogram deriving step that derives, based on a difference between the first group delay and the second group delay, a sinogram for a difference in the group delay between the first device under test and the second device under test; a delay period recording step that records a delay period of the electromagnetic wave caused by a transmission of the electromagnetic wave through the container; a delay-corrected sinogram deriving step that derives a delay-corrected sinogram obtained by subtracting the delay period from the sinogram; and an image deriving step that derives, based on the delay-corrected sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a sinogram deriving step that derives a first sinogram based on the first group delay, and a second sinogram based on the second group delay; a delay period recording step that records a delay period of the electromagnetic wave caused by a transmission of the electromagnetic wave through the container; a delay-corrected sinogram deriving step that derives a delay-corrected sinogram obtained by subtracting the delay period from the first sinogram; and an image deriving step that derives an image of a cross section of the first device under test based on the delay-corrected sinogram, and an image of a cross section of the second device under test based on the second sinogram, and, as a difference between the image of the cross section of the first device under test and the image of the cross section of second device under test, derives an image representing a difference in the group delay between the first device under test and the second device under test.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a chromatic dispersion deriving step that derives, based on a derived result by the phase deriving step, a chromatic dispersion in the frequency domain of the electromagnetic wave which has transmitted through the device under test; a sinogram deriving step that derives a sinogram based on a derived result by the chromatic dispersion deriving step; a delay period recording step that records a delay period of the electromagnetic wave caused by a transmission of the electromagnetic wave through the container; a delay-corrected sinogram deriving step that derives a delay-corrected sinogram obtained by subtracting a value, which is obtained by partially differentiating the group delay with respect to the frequency, from the sinogram; and an image deriving step that derives, based on the delay-corrected sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a transmittance recording step that records a value representing a transmittance of a power of the electromagnetic wave transmitting through the container while a reflection of the electromagnetic wave on a transmission surface through which the electromagnetic wave transmits in the container is considered; a corrected power deriving step that derives a corrected power which is a power of the electromagnetic wave detected when the transmittance is 100% based on a power of the electromagnetic wave detected by the electromagnetic wave detector and the transmittance; an attenuation ratio deriving step that derives an attenuation ratio of the electromagnetic wave which has transmitted through the device under test based on the corrected power; and an inverse radon transform step that applies the inverse radon transform to a derived result by the attenuation ratio deriving step.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a group delay deriving step that derives, based on a derived result by the phase deriving step, a group delay in the frequency domain of the electromagnetic wave which has transmitted through the device under test; a delay period recording step that records a delay period of the electromagnetic wave caused by a transmission of the electromagnetic wave through the container; a group delay correction step that derives a corrected group delay obtained by subtracting the delay period from the group delay; a sinogram deriving step that derives a sinogram based on the corrected group delay; and an image deriving step that derives, based on the sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changing unit that changes a relative position of a first intersection at which an optical path of the electromagnetic wave transmitting through the first device under test and the first device under test intersect with respect to the first device under test, the measurement process including: a phase deriving step that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test; a group delay deriving step that derives, based on a derived result by the phase deriving step, a first group delay in the frequency domain of the electromagnetic wave which has transmitted through the first device under test, and a second group delay in the frequency domain of the electromagnetic wave which has transmitted through the second device under test; a delay period recording step that records a delay period of the electromagnetic wave caused by a transmission of the electromagnetic wave through the container; a group delay correction step that derives a corrected group delay obtained by subtracting the delay period from the first group delay; a sinogram deriving step that derives, based on a difference between the corrected group delay and the second group delay, a sinogram for a difference in the group delay between the first device under test and the second device under test; and an image deriving step that derives, based on the sinogram, an image of a cross section of the device under test including the intersection.

The present invention is a computer-readable medium having a program of instructions for execution by a computer to perform a measurement process using an electromagnetic wave measurement device having an electromagnetic wave output device that outputs an electromagnetic wave having a frequency equal to or more than 0.01 [THz] and equal to or less than 100 [THz] toward a device under test and a container storing at least a part of the device under test; an electromagnetic wave detector that detects the electromagnetic wave which has transmitted through the device under test; and a relative position changing unit that changes a relative position of an intersection at which an optical path of the electromagnetic wave transmitting through the device under test and the device under test intersect with respect to the device under test, the measurement process including: a phase deriving step that derives, based on a detected result by the electromagnetic wave detector, a phase in the frequency domain of the electromagnetic wave which has transmitted through the device under test; a chromatic dispersion deriving step that derives, based on a derived result by the phase deriving step, a chromatic dispersion in the frequency domain of the electromagnetic wave which has transmitted through the device under test; a delay period recording step that records a delay period of the electromagnetic wave caused by a transmission of the electromagnetic wave through the container; a chromatic dispersion correction step that derives a corrected chromatic dispersion obtained by subtracting a value, which is obtained by partially differentiating the group delay with respect to the frequency, from the chromatic dispersion; a sinogram deriving step that derives a sinogram based on the corrected chromatic dispersion; and an image deriving step that derives, based on the sinogram, an image of a cross section of the device under test including the intersection.

BEST MODE FOR CARRYING OUT THE INVENTION

A description will now be given of embodiments of the present invention with reference to drawings.

First Embodiment

Figure 1:
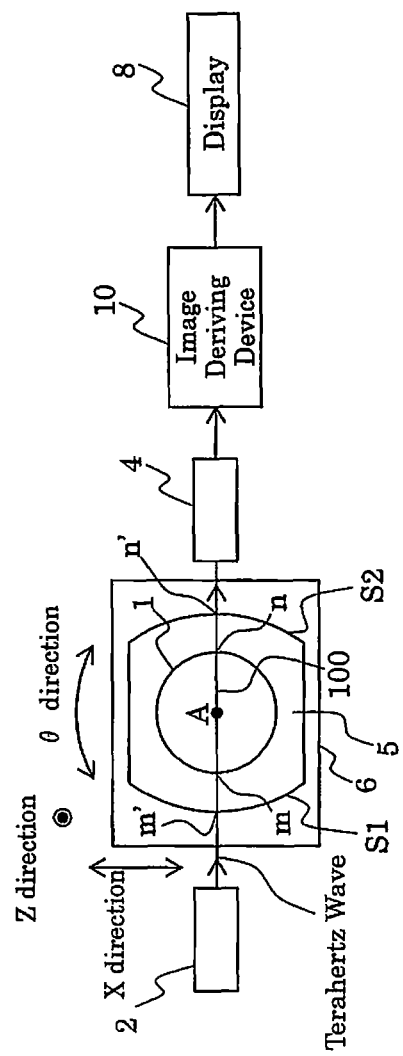
FIG. 1 is a diagram showing a configuration of an electromagnetic wave measurement device according to a first embodiment of the present invention.
Figure 2:
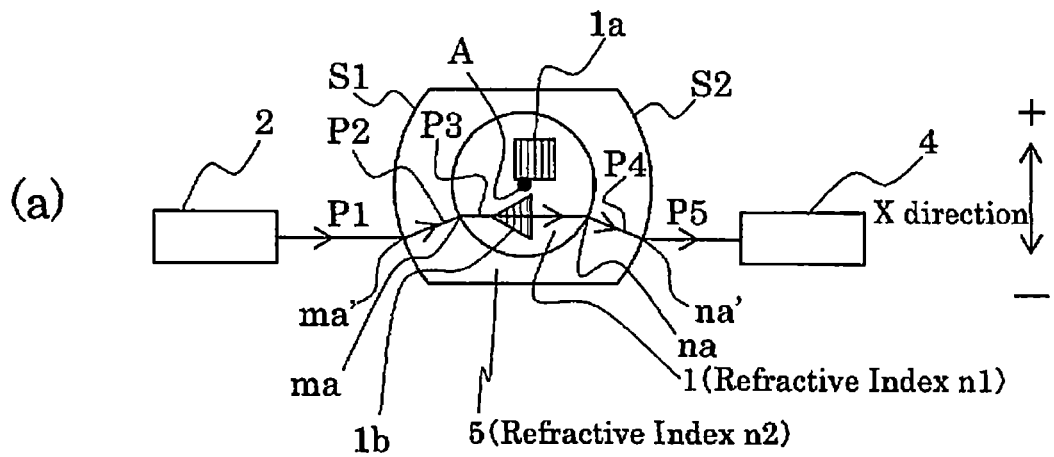
FIGS. 2(a) and 2(b) are plan views of the DUT 1, the electromagnetic wave output device 2, and the electromagnetic wave detector 4 when the stage for scanning 6 is moved in the X direction.
Figure 2:
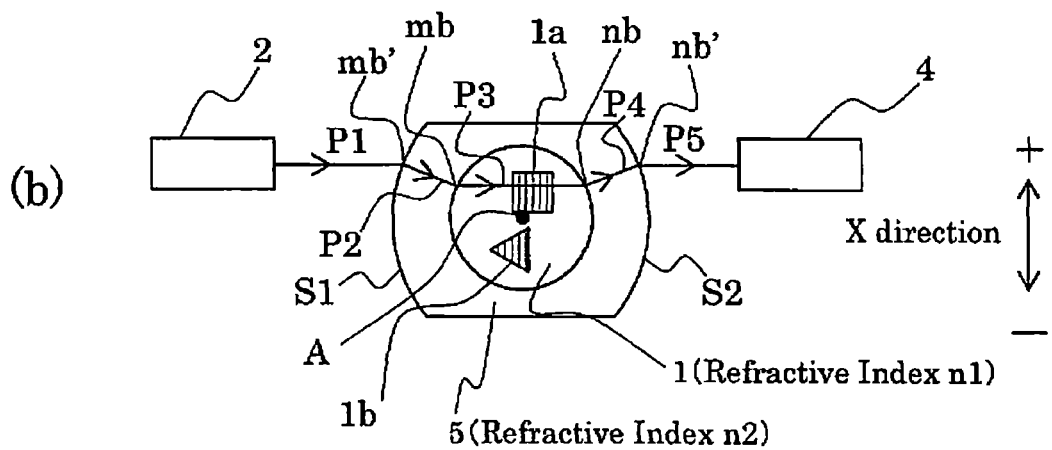

FIG. 1 is a diagram showing a configuration of an electromagnetic wave measurement device according to a first embodiment of the present invention. The electromagnetic wave measurement device according to the first embodiment includes an electromagnetic wave output device 2, an electromagnetic wave detector 4, a stage for scanning (relative position changing unit) 6, a display 8, and an image deriving device 10. The electromagnetic wave measurement device is used for measuring a device under test (DUT) 1.

A container 5 stores at least a part of the DUT 1 to be measured by the terahertz wave measurement device. FIG. 1 shows a planar cross section of the DUT 1 and the container 5. The DUT 1 is cylindrical, for example.

Figure 12:
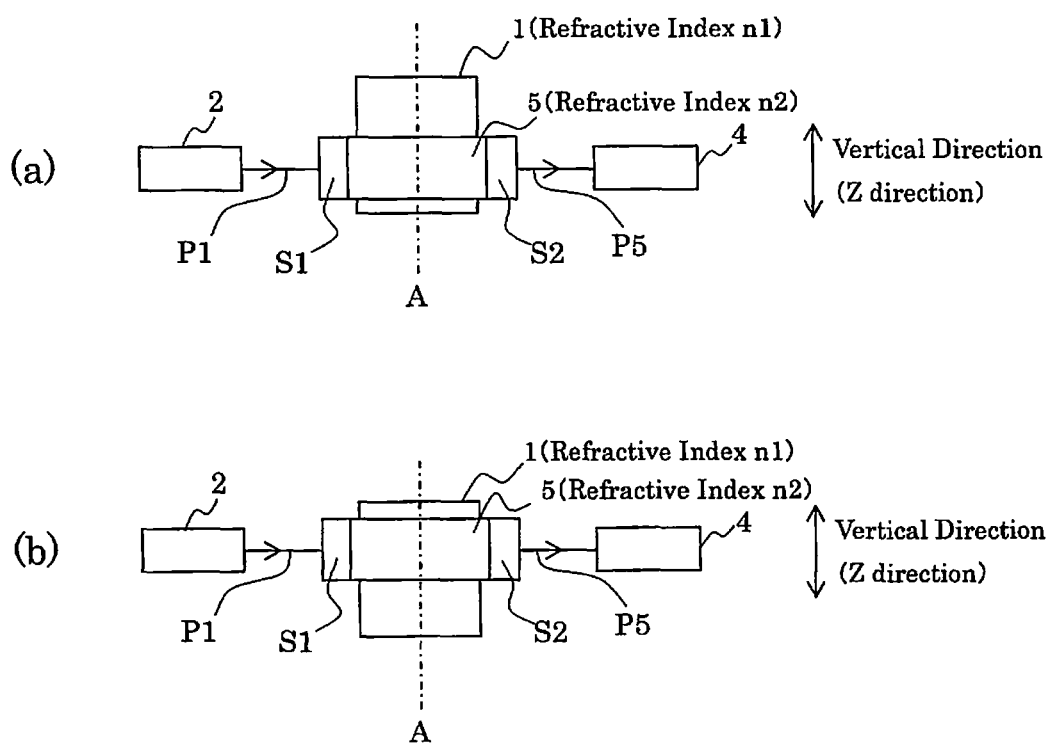
FIGS. 12(a) and 12(b) are front views of the container 5 storing a part of the DUT 1, and the terahertz wave measurement device.
Figure 13:
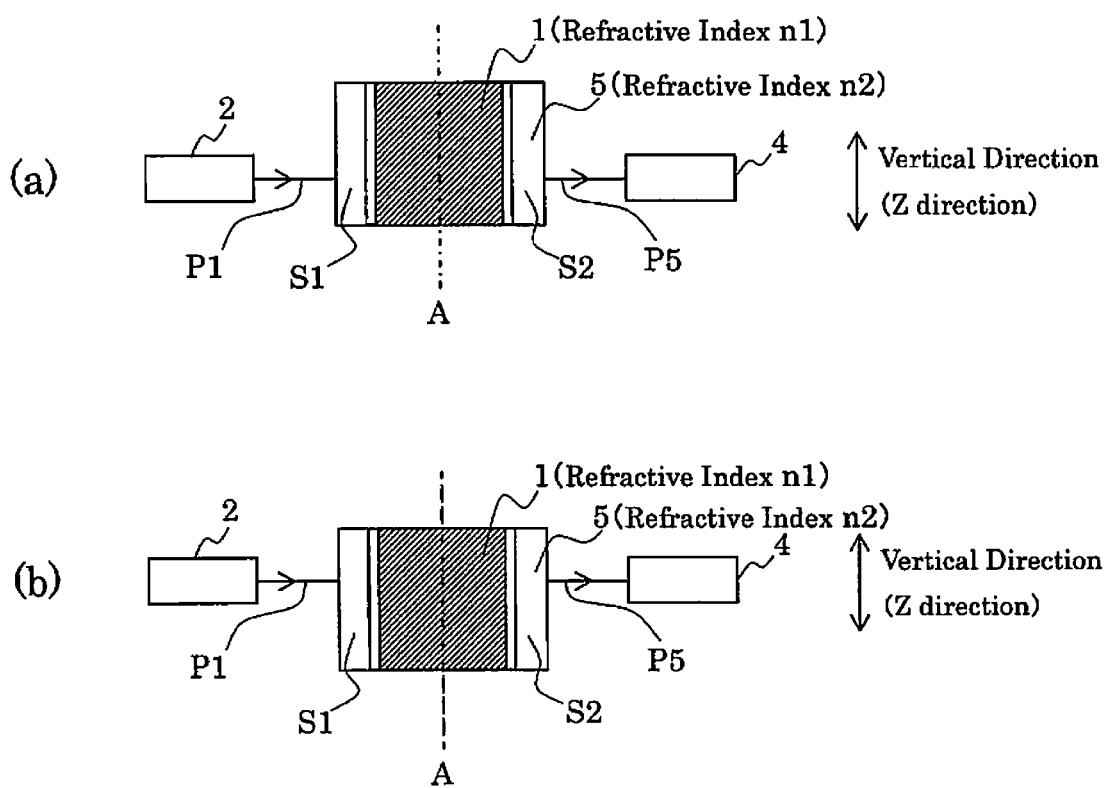
FIGS. 13(a) and 13(b) are front views of the container 5 storing an entirety of the DUT 1, and the terahertz wave measurement device.

Moreover, the container 5 may store the DUT 1 partially (refer to FIGS. 12(a) and 12(b)) or entirely (refer to FIGS. 13(a) and 13(b)).

Further, though there is a slight gap between the container 5 and the DUT 1, the gap is not illustrated The electromagnetic wave output device 2 outputs an electromagnetic wave having a frequency equal to or more than 0.01 [THz] and equal to or less than 100 [THz] toward the DUT 1 and the container 5. The frequency of the electromagnetic wave output toward the DUT 1 includes a terahertz wave band (such as equal to or more than 0.03 [THz] and equal to or less than 10 [THz]). According to the embodiment of the present invention, it is assumed to employ a terahertz wave as an example of the electromagnetic wave.

The terahertz wave output toward the DUT 1 transmits through the DUT 1. The electromagnetic wave detector 4 detects the electromagnetic wave (such as a terahertz wave) which has transmitted through the DUT 1.

A point at which the terahertz wave is made incident to the DUT 1 is m, and a point at which the terahertz wave is emitted from the DUT 1 is n. Then, an intersection 100 between an optical path of the electromagnetic wave which transmits through the DUT 1 and the DUT 1 is represented as a line mn. Moreover, a planar cross sectional shape of the DUT 1 is circular, and the center of the circle is a point A.

Further, a point at which the terahertz wave is made incident to the container 5 is m', and a point at which the terahertz wave is emitted from the container 5 is n'.

All points ma, mb, mc, and md in FIGS. 2(a), 2(b), 3(a), and 3(b) are points at which the terahertz wave is made incident to the DUT 1. All points na, nb, nc, and nd in FIGS. 2(a), 2(b), 3(a), and 3(b) are points at which the terahertz wave is emitted from the DUT 1.

All points ma', mb', mc', and md' in FIGS. 2(a), 2(b), 3(a), and 3(b) are points at which the terahertz wave is made incident to the container 5. All points na', nb', nc', and nd' in FIGS. 2(a), 2(b), 3(a), and 3(b) are points at which the terahertz wave is emitted from the container 5.

The container 5 includes a first curved surface portion S1 and a second curved surface portion S2. The first curved surface portion S1 is a cylindrical surface with a radius of r1 (a part of a side surface of a cylinder the bottom surface of which is a circle with the radius of r1). The second curved surface portion S2 is a cylindrical surface with a radius of r2 (a part of a side surface of a cylinder the bottom surface of which is a circle with the radius of r2). There holds a relationship r2=r1. The first curved surface portion S1 and the second curved surface portion S2 are illustrated as arcs which are line-symmetric with each other in FIG. 1

The DUT 1 is arranged between the first curved surface portion S1 and the second curved surface portion S2. On this occasion, a refractive index of the DUT 1 is denoted by n1, and a refractive index of the container 5 is denoted by n2. Then, a relationship n1<n2 holds. Moreover, both the first curved surface portion S1 and the second curved surface portion S2 are convex surfaces. Further, n1 and n2 may not be equal to the refractive index (such as 1) of ambient air of the container 5.

It should be noted that the material of the container 5 may be a resin material such as Teflon (registered trademark), polyethylene, and the like. These resin materials cannot usually be used for measurement of a light ray in the visible light area or the infrared light area. However, these resin materials present a little absorption and scatter of the light ray of the terahertz wave, and can thus be used for measurement by means of the terahertz wave.

The stage for scanning (relative position changing unit) 6 changes a relative position of the intersection 100 with respect to the DUT 1. For example, the DUT 1 is fixed to the stage for scanning 6, the stage for scanning 6 moves in an X direction and a Z direction (direction perpendicular to the sheet of FIG. 1), and rotates about a line which passes through the point A, and is perpendicular to the sheet of FIG. 1 (referred to as "movement in a θ direction").

FIGS. 2(a) and 2(b) are plan views of the DUT 1, the electromagnetic wave output device 2, and the electromagnetic wave detector 4 when the stage for scanning 6 is moved in the X direction. It should be noted that the DUT 1 contains contents 1a and 1b. The stage for scanning 6 is not illustrated.

Referring to FIG. 2(a), when the stage for scanning 6 is moved in the +X direction from the state shown in FIG. 1 (alternatively the electromagnetic wave output device 2 and the electromagnetic wave detector 4 may be moved in the −X direction), the intersection 100 is represented by a line mana. The relative position of the intersection 100 with respect to the DUT 1 is below the point A. The intersection 100 passes through the content 1b.

Referring to FIG. 2(b), when the stage for scanning 6 is moved in the −X direction from the state shown in FIG. 1 (alternatively the electromagnetic wave output device 2 and the electromagnetic wave detector 4 may be moved in the +X direction), the intersection 100 is represented by a line mbnb. The relative position of the intersection 100 with respect to the DUT 1 is above the point A. The intersection 100 passes through the content 1a.

When the stage for scanning 6 is moved in the X direction, thereby changing the state from that shown in FIG. 2(a) to that shown in FIG. 2(b), the relative position of the intersection 100 with respect to the DUT 1 changes from that below the point A to that above the point A.

Referring to FIG. 2(b), a description will be given of an optical path of the terahertz wave output from the terahertz wave output device 2.

First, the terahertz wave output from the terahertz wave output device 2 (optical path P1) is irradiated on the first curved surface portion S1. On this occasion, the terahertz wave refracts. In other words, the container 5 (1<n2) serves as a convex lens, and the optical path thus turns toward in the −X direction, and travels on an optical path P2 (line mb'mb) in the container 5. The terahertz wave which has traveled on the optical path P2 is made incident to the DUT 1, and refracts. In other words, the optical path is turned in the +X direction with respect to an extension of the optical path P2 by the DUT 1 (n1<b2), and the terahertz wave travels on an optical path P3 (line mbnb). The optical path P3 is approximately parallel with the optical path P1 and the optical axis OA.

The terahertz wave which has traveled on the optical path P3 in the DUT 1 is made incident to the container 5, and refracts. In other words, the optical path turns in the +X direction by the container 5, and the terahertz wave travels on an optical path P4 (line nbnb'). The terahertz wave which has traveled on the optical path P4 is made incident to the second curved surface portion S2, and refracts. In other words, the container 5 (1<n2) serves as a convex lens, and the terahertz wave travels on an optical path P5, and is made incident to the terahertz wave detector 4.

In FIG. 2(b), since the arc representing the first curved surface portion S1 and the arc representing the second curved surface portion S2 are line symmetrical, the optical path P2 is approximately line symmetrical with the optical path P4, and the optical path P1 is approximately line symmetrical with the optical path P5. Thus, the optical path P5 is approximately located on an extension of the optical path P1.

Figure 3:
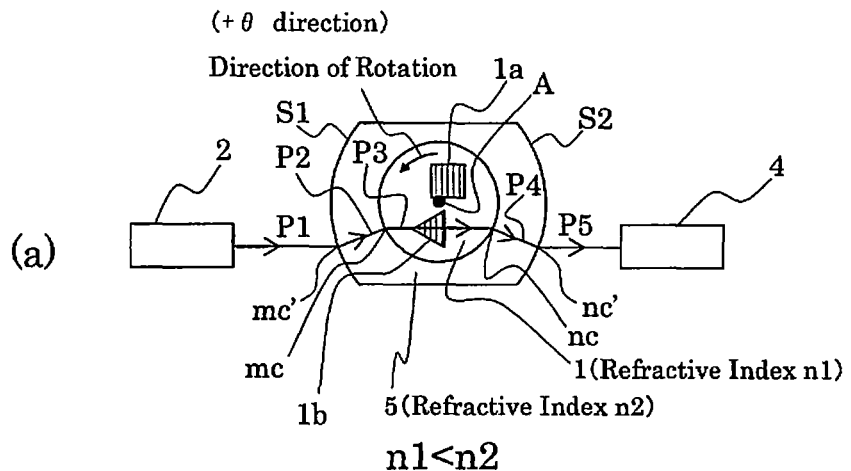
FIG. 3(a) is a plan view of the DUT 1, the electromagnetic wave output device 2, and the electromagnetic wave detector 4 when the stage for scanning 6 is not moved in the θ direction.
FIG. 3(b) is a plan view of the DUT 1, the electromagnetic wave output device 2, and the electromagnetic wave detector 4 when the stage for scanning 6 is moved in the +θ direction.
Figure 3:
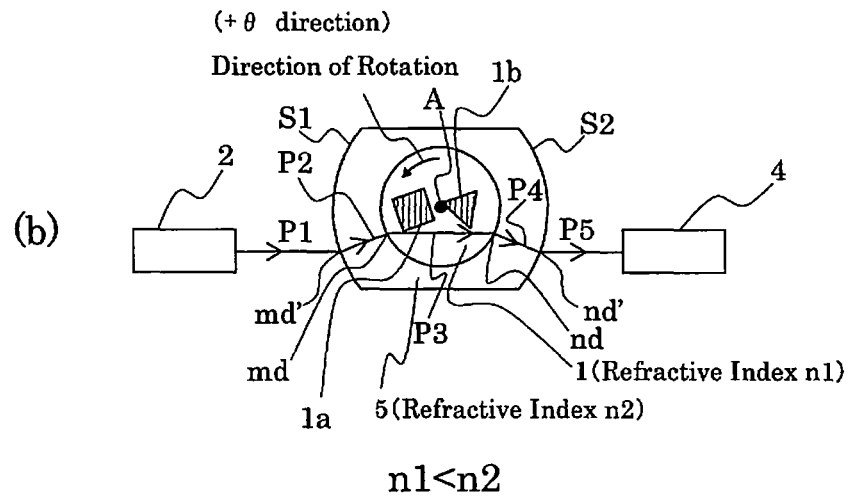

FIG. 3(a) is a plan view of the DUT 1, the electromagnetic wave output device 2, and the electromagnetic wave detector 4 when the stage for scanning 6 is not moved in the θ direction, and FIG. 3(b) is a plan view of the DUT 1, the electromagnetic wave output device 2, and the electromagnetic wave detector 4 when the stage for scanning 6 is moved in the +θ direction. It should be noted that the DUT 1 contains the contents 1a and 1b. The stage for scanning 6 is not illustrated. Moreover, as a result of the rotation in the +θ direction of the stage for scanning 6, the DUT 1 rotates in the +θ direction while the container 5 does not rotate.

Referring to FIG. 3(a), when the stage for scanning 6 is not moved in the θ direction, the same state as that in FIG. 2(a) arises, and the intersection 100 is thus represented by the line mcnc. The intersection 100 passes through the content 1b.

Referring to FIG. 3(b), when the stage for scanning 6 is moved in the +θ direction from the state shown in FIG. 3(a) (alternatively, the electromagnetic wave output device 2 and the electromagnetic wave detector 4 may be moved in the −θ direction), the intersection 100 is represented by a line mdnd. The intersection 100 does not transmit through either the content 1a or 1b.

When the stage for scanning 6 is moved in the θ direction, thereby changing the state from that shown in FIG. 3(a) to that shown in FIG. 3(b), the relative position of the intersection 100 with respect to the DUT 1 changes.

FIGS. 12(a) and 12(b) are front views of the container 5 storing a part of the DUT 1, and the terahertz wave measurement device. The DUT 1 is cylindrical, and a part of the DUT 1 is stored in the container 5. The optical paths P2, P3, and P4 are omitted from the FIGS. 12(a) and 12(b).

The container 5 and the optical paths P1 and P5 of the terahertz wave move in a vertical direction (downward in FIGS. 12(a) and 12(b)) with respect to the DUT 1. Then, the optical path P5 intersects with a lower part of the DUT 1 as shown in FIG. 12(a). As a result, the lower part of the DUT 1 is measured by the terahertz wave measurement device. It is only necessary, for moving the optical paths P1 and P5 of the terahertz wave, to move the terahertz wave output device 2 and the terahertz wave detector 4.

The container 5 and the optical paths P1 and P5 of the terahertz wave move in the vertical direction (upward in FIGS. 12(a) and 12(b)) with respect to the DUT 1. Then, the optical path P5 intersects with an upper part of the DUT 1 as shown in FIG. 12(b). As a result, the upper part of the DUT 1 is measured by the terahertz wave measurement device. It is only necessary, for moving the optical paths P1 and P5 of the terahertz wave, to move the terahertz wave output device 2 and the terahertz wave detector 4.

The DUT 1 may vertically be moved with respect to the container 5 and the optical paths P1 and P5 of the terahertz wave.

FIGS. 13(a) and 13(b) are front views of the container 5 storing an entirety of the DUT 1, and the terahertz wave measurement device. It should be noted that only the DUT 1 is shown as a cross section. The DUT 1 is cylindrical, and the entirely of the DUT 1 is stored in the container 5. The optical paths P2, P3, and P4 are omitted from the FIGS. 13(a) and 13(b).

Referring to FIG. 13(a), the container 5 and the DUT 1 move in the vertical direction (upward in FIGS. 13(a) and 13(b)) with respect to the optical paths P1 and P5 of the terahertz wave. As a result, the lower part of the DUT 1 is measured by the terahertz wave measurement device.

Referring to FIG. 13(b), the container 5 and the DUT 1 move in the vertical direction (downward in FIGS. 13(a) and 13(b)) with respect to the optical paths P1 and P5 of the terahertz wave. Then, the upper part of the DUT 1 is measured by the terahertz wave measurement device.

The optical paths P1 and P5 of the terahertz wave may vertically be moved with respect to the container 5 and the DUT 1.

As described above, the DUT 1 can be scanned by the stage for scanning 6.

The image deriving device 10 derives an image of a cross section of the DUT 1 made on a plane containing the intersection 100 (the sheet in FIGS. 1, 2(a), 2(b), 3(a), and 3(b)).

The display 8 shows an image F(x, y) (refer to an equation (5)) derived by the image deriving device 10. The derived image is numerical data on the two-dimensional cross section of the DUT 1, and a two-dimensional tomographic image of the DUT 1 is shown by associating the numerical data with predetermined colors. It should be noted that a widely known method may be properly employed as the method for displaying the two-dimensional tomographic image based on the numerical data.

Figure 4:
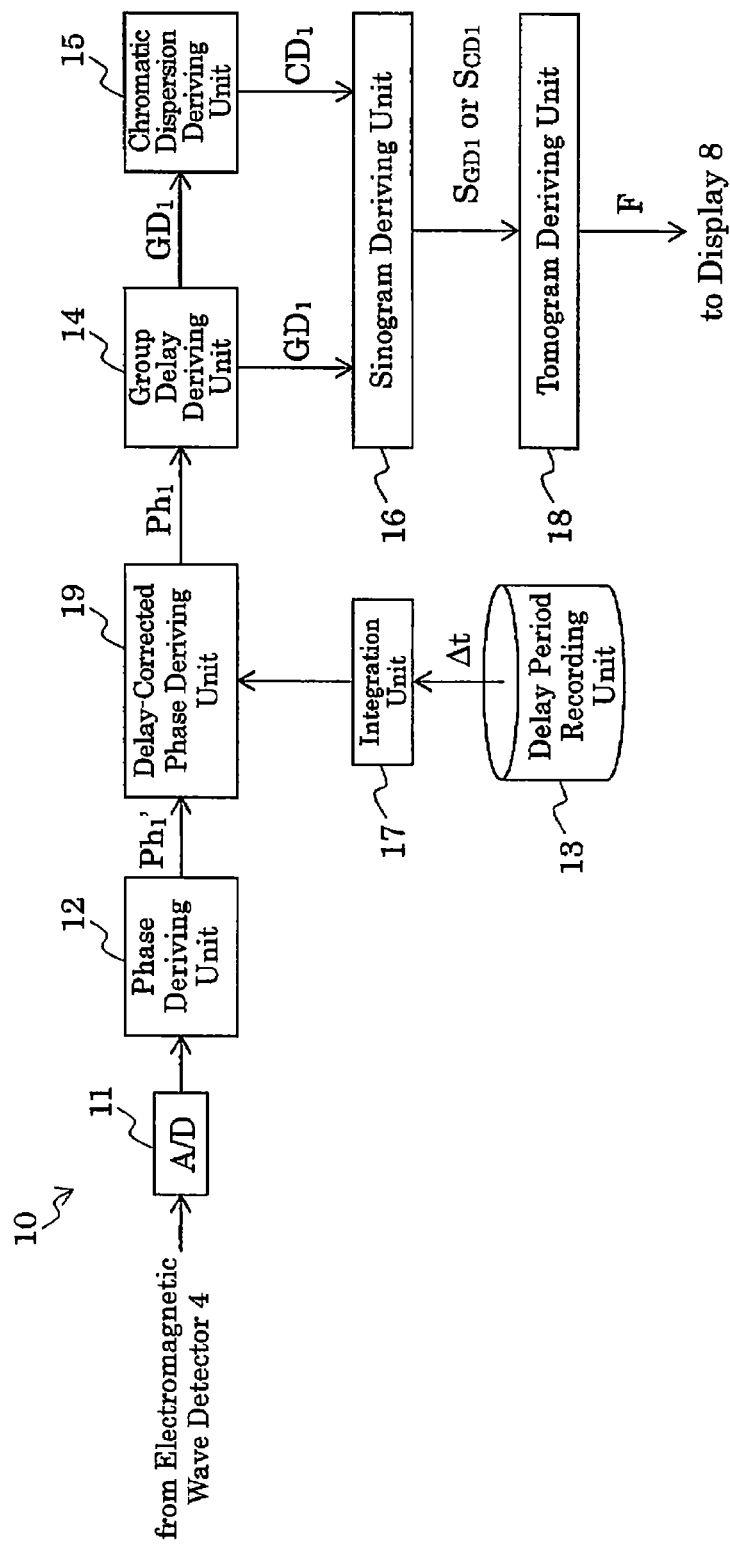
FIG. 4 is a functional block diagram showing a configuration of the image deriving device 10 according to the first embodiment.

FIG. 4 is a functional block diagram showing a configuration of the image deriving device 10 according to the first embodiment. The image deriving device 10 includes an A/D converter 11, a phase deriving unit 12, a delay period recording unit 13, a group delay deriving unit 14, a chromatic dispersion deriving unit 15, a sinogram deriving unit 16, an integration unit 17, a tomogram deriving unit (image deriving unit) 18, and a delay-corrected phase deriving unit 19.

The A/D converter 11 converts a detected result by the electromagnetic wave detector 4, which is an analog signal, into a digital signal.

The phase deriving unit 12 derives a phase in the frequency domain of the electromagnetic wave (such as a terahertz wave) which has transmitted through the DUT 1 based on the detected result by the electromagnetic wave detector 4.

The phase deriving unit 12 receives the output of the A/D converter 11. The output of the A/D converter 11 is pulse waveform data of the electromagnetic wave which has transmitted through the DUT 1. The pulse waveform data is a function of x (movement in the X direction of the stage for scanning 6), θ (movement in the θ direction of the stage for scanning 6), and t (time).

The phase deriving unit 12 transforms this pulse waveform data by the Fourier transform, thereby acquiring spectrum data of the pulse waveform in the frequency domain. The spectrum data of the pulse waveform is a function of x, θ, and f (frequency). The phase deriving unit 12 derives a phase $Ph_1'(x, \theta, f)$ from the spectrum data of the pulse waveform. It should be noted that arguments (x, θ, f) of the function $Ph_1'(x, \theta, f)$ are omitted in FIG. 4. For other functions, illustration of arguments is omitted similarly.

The delay period recording unit 13 records a delay period $\Delta t(x, \theta)$ of the electromagnetic wave (such as a terahertz wave) caused by the transmission of the electromagnetic wave through the container 5. The delay period $\Delta t(x, \theta)$ causes an error of the phase $Ph_1'(x, \theta, f)$ derived by the phase deriving unit 12.

The delay period $\Delta t(x, \theta)$ is represented, referring to FIG. 1, as follows.

$\Delta t(x,\theta)$=(((refractive index of optical path $mm'$)−1)
$mm'$+((refractive index of optical path $nn'$)−1)
$nn'$)/c where c denotes the velocity of light.

The refractive index of the container 5 is n2, and the following equation thus holds:

$\Delta t(x,\theta)$=((n2−1)$mm'$+(n2−1)$nn'$)/c

The integration unit 17 integrates the delay period $\Delta t(x, \theta)$ with respect to the frequency f.

The delay-corrected phase deriving unit 19 subtracts the output (value obtained by integrating the delay period $\Delta t(x, \theta)$ with respect to the frequency f) of the integration unit 17 from the phase $Ph_1'(x, \theta, f)$ derived by the phase deriving unit 12, thereby deriving a delay-corrected phase $Ph_1(x, \theta, f)$. The delay-corrected phase $Ph_1(x, \theta, f)$ has a value obtained by removing the error caused by the delay period $\Delta t(x, \theta)$ from the phase $Ph_1'(x, \theta, f)$.

The group delay deriving unit 14 receives the delay-corrected phase $Ph_1(x, \theta, f)$ from the delay-corrected phase deriving unit 19, and derives a group delay $GD_1(x, \theta, f)$ in the frequency domain of the electromagnetic wave which has transmitted through the DUT 1 based on the delay-corrected phase $Ph_1(x, \theta, f)$.

It should be noted that the group delay $GD_1(x, \theta, f)$ is derived by the group delay deriving unit 14 according to the following equation (1).

$$GD_1(x, \theta, f) = \frac{\partial}{\partial f} Ph_1(x, \theta, f) \quad \text{Equation (1)}$$

The chromatic dispersion deriving unit 15 derives a chromatic dispersion in the frequency domain of the electromagnetic wave which has transmitted through the DUT 1 based on a derived result by the delay-corrected phase deriving unit 19.

Specifically, the chromatic dispersion deriving unit 15 receives the group delay $GD_1(x, \theta, f)$ from the group delay deriving unit 14, and derives a chromatic dispersion $CD_1(x, \theta, f)$ in the frequency domain of the electromagnetic wave which has transmitted through the DUT 1.

It should be noted that the chromatic dispersion $CD_1(x, \theta, f)$ is represented by the following equation (2), and it is thus appreciated that the chromatic dispersion $CD_1(x, \theta, f)$ can be obtained by partially differentiating the group delay $GD_1(x, \theta, f)$ with respect to the frequency f.

It should be noted that the chromatic dispersion deriving unit 15 may receive the delay-corrected phase $Ph_1(x, \theta, f)$ from the delay-corrected phase deriving unit 19, may assign the delay-corrected phase $Ph_1(x, \theta, f)$ to the equation (2), and may derive the chromatic dispersion $CD_1(x, \theta, f)$.

$$CD_1(x, \theta, f) = \frac{\partial^2}{\partial f^2} Ph_1(x, \theta, f) \quad \text{Equation (2)}$$

The sinogram deriving unit 16 derives a sinogram based on the derived result (delay-corrected phase $Ph_1(x, \theta, f)$) by the delay-corrected phase deriving unit 19.

Specifically, the sinogram deriving unit 16 receives the group delay $GD_1(x, \theta, f)$ from the group delay deriving unit 14, and derives the sinogram $S_{GD1}(x, \theta)$ for the group delay as shown in the following equation (3). Since the group delay $GD_1(x, \theta, f)$ is derived based on the delay-corrected phase $Ph_1(x, \theta, f)$ (refer to the equation (1)), the sinogram $S_{GD1}(x, \theta)$ is also derived based on the delay-corrected phase $Ph_1(x, \theta, f)$.

$$S_{GD1}(x,\theta) = \int GD_1(x,\theta,f) df \quad \text{Equation (3)}$$

Alternatively, the sinogram deriving unit 16 receives the chromatic dispersion $CD_1(x, \theta, f)$ from the chromatic dispersion deriving unit 15, and derives the sinogram $S_{CD1}(x, \theta)$ for the chromatic dispersion as shown in the following equation (4). Since the chromatic dispersion $CD_1(x, \theta, f)$ is derived based on the delay-corrected phase $Ph_1(x, \theta, f)$ (refer to the equation (2)), the sinogram $S_{CD1}(x, \theta)$ is also derived based on the delay-corrected phase $Ph_1(x, \theta, f)$.

$$S_{CD1}(x,\theta) = \int CD_1(x,\theta,f) df \quad \text{Equation (4)}$$

The tomogram deriving unit (image deriving unit) 18 receives the sinogram from the sinogram deriving unit 16, and derives an image of the cross section of the DUT 1 including the intersection 100 based on the sinogram.

When the sinogram derived by the sinogram deriving unit 16 is represented as $S(x, \theta)$, the tomogram deriving unit 18 derives the image $F(x, y)$ as described by the following equation (5). The equation (5) implies derivation of the image according to the filtered back projection.

$$F(x, y) = \frac{1}{4\pi} \int_0^{2\pi} \left\{ \frac{1}{2\pi} \int_{-\infty}^{+\infty} \left[ \int_{-\infty}^{+\infty} S(x, \theta) e^{-i\omega x} dx \right] |\omega| e^{i\omega x} d\omega \right\} d\theta \quad \text{Equation (5)}$$

A description will now be given of an operation of the first embodiment.

First, the DUT 1 is fixed to the stage for scanning 6. Then, while the stage for scanning 6 is moving in the X direction and the Z direction (direction perpendicular to the sheet of FIG. 1) as well as the θ direction, the electromagnetic wave output device 2 outputs the electromagnetic wave having a frequency equal to or more than 0.01 [THz] and equal to or less than 100 [THz] (such as a terahertz wave) toward the DUT 1. The terahertz wave output toward the DUT 1 transmits through the DUT 1. The electromagnetic wave which has transmitted through the DUT 1 is detected by the electromagnetic wave detector 4. In this way, the DUT 1 is scanned.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_1'(x, \theta, f)$ in the frequency domain of the electromagnetic wave which has transmitted through the DUT 1. The phase $Ph_1'(x, \theta, f)$ contains the error caused by the delay of the electromagnetic wave (such a terahertz wave) which is a result of the electromagnetic wave transmitting though the container 5.

The delay-corrected phase deriving unit 19 subtracts the output (value obtained by integrating the delay period $\Delta t(x, \theta)$ recorded in the delay period recording unit 13 with respect to the frequency f) of the integration unit 17 from the phase $Ph_1'(x, \theta, f)$ derived by the phase deriving unit 12. As a result, the delay-corrected phase $Ph_1(x, \theta, f)$ from which the error caused by the delay of the electromagnetic wave as a result of the electromagnetic wave transmitting through the container 5 has been removed is derived.

The group delay $GD_1(x, \theta, f)$ and the chromatic dispersion $CD_1(x, \theta, f)$ are derived based on the delay-corrected phase $Ph_1(x, \theta, f)$, and are fed to the sinogram deriving unit 16.

The sinogram deriving unit 16 derives the sinogram $S_{GD1}(x, \theta)$ based on the group delay, or the sinogram $S_{CD1}(x, \theta)$ based on the chromatic dispersion. The tomogram deriving unit 18 derives the image of the cross section of the DUT 1 from the derived sinogram.

The display 8 shows the image derived by the image deriving device 10.

According to the first embodiment, when the CT is carried out for the DUT 1 stored in the container 5 based on the phase $Ph_1'(x, \theta, f)$ (specifically, based on the group delay or the chromatic dispersion), it is possible to remove the error caused by the delay of the electromagnetic wave as a result of the electromagnetic wave transmitting through the container 5 from the phase $Ph_1'(x, \theta, f)$.

Second Embodiment

A second embodiment is different from the first embodiment in that the (first) DUT 1 and a second DUT 20 are used. The DUT 1 according to the first embodiment is referred to as a first DUT 1 according to the second embodiment.

Figure 5:
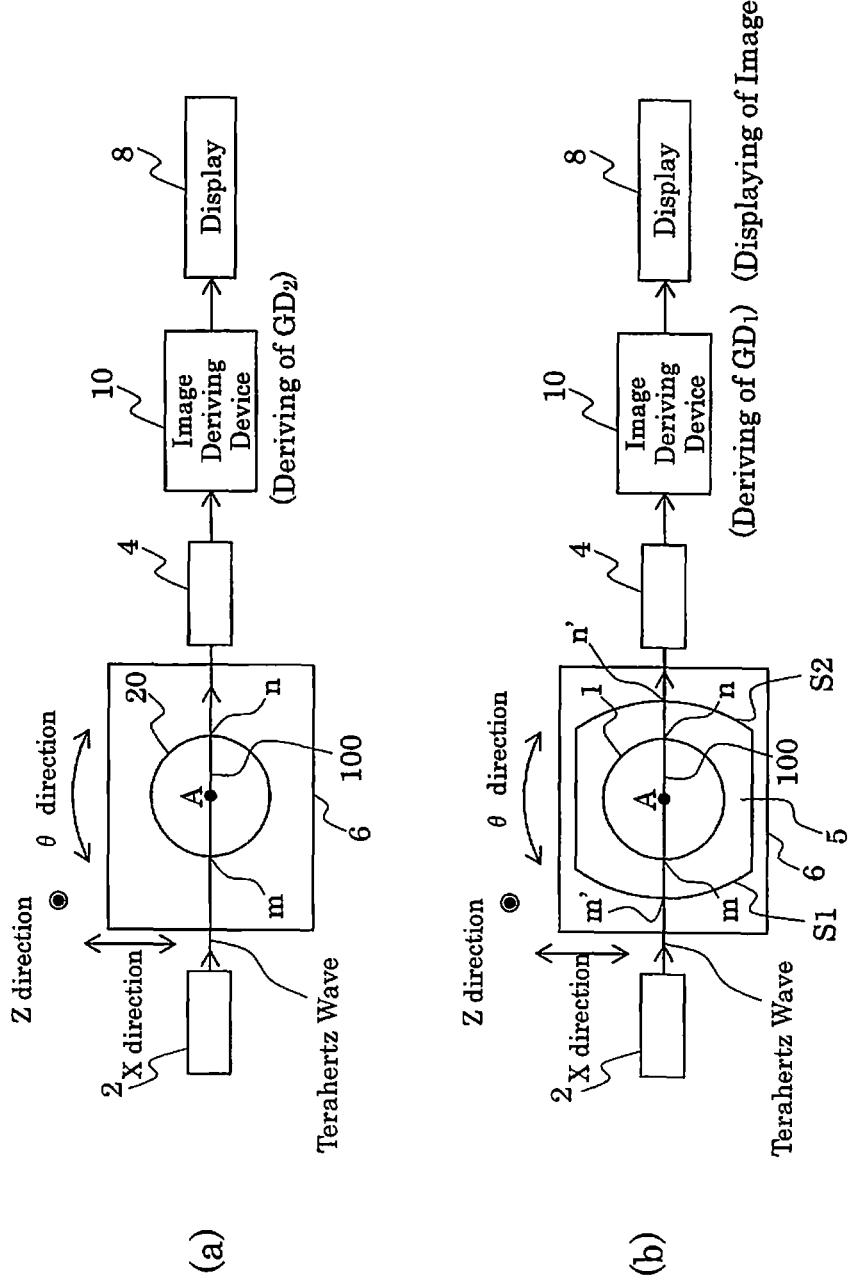
FIGS. 5(a) and 5(b) are diagrams showing a configuration of the electromagnetic wave measurement device according to the second embodiment.
Figure 6:
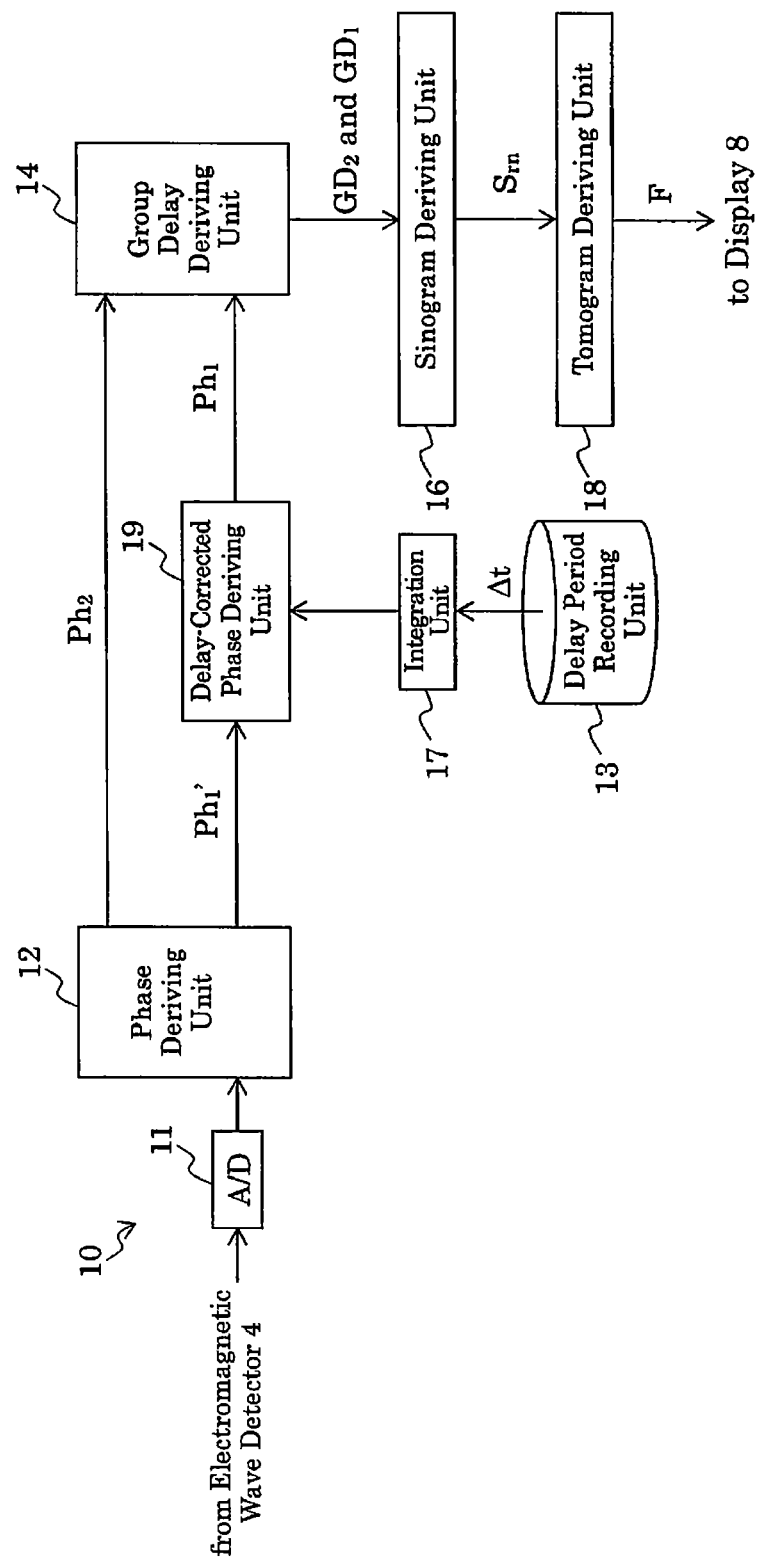
FIG. 6 is a functional block diagram showing a configuration of the image deriving device 10 according to the second embodiment.

FIGS. 5(*a*) and 5(*b*) are diagrams showing a configuration of the electromagnetic wave measurement device according to the second embodiment. FIG. 6 is a functional block diagram showing a configuration of the image deriving device 10 according to the second embodiment. In the following section, the same components are denoted by the same numerals as of the first embodiment, and will be explained in no more details.

The electromagnetic wave measurement device according to the second embodiment includes the electromagnetic wave output device 2, the electromagnetic wave detector 4, the stage for scanning (relative position changing unit) 6, the display 8, and the image deriving device 10. The electromagnetic wave measurement device is used for measuring the DUT 1.

Moreover, the image deriving device 10 according to the second embodiment includes the A/D converter 11, the phase deriving unit 12, the delay period recording unit 13, the group delay deriving unit 14, the sinogram deriving unit 16, the integration unit 17, the tomogram deriving unit (image deriving unit) 18, and the delay-corrected phase deriving unit 19.

The container 5 is the same as that of the first embodiment, and hence a description thereof is omitted. The (first) DUT 1 is the same as the DUT 1 of the first embodiment, and hence a description thereof is omitted.

The second DUT 20 (refer to FIG. 5(*a*)) is not stored in the container 5.

The electromagnetic wave output device 2 is the same as that of the first embodiment (refer to FIG. 5(*b*)). However, the electromagnetic wave output device 2 further outputs an electromagnetic wave (same as the electromagnetic wave fed toward the first DUT 1) toward the second DUT 20 (refer to FIG. 5(*a*)).

The electromagnetic wave detector 4 is the same as that of the first embodiment (refer to FIG. 5(*b*)). However, the electromagnetic wave detector 4 also detects the electromagnetic wave (such as a terahertz wave) which has transmitted through the second DUT 20 (refer to FIG. 5(*a*)).

The stage for scanning (relative position changing unit) 6 is the same as that of the first embodiment (refer to FIG. 5(*b*)). However, the stage for scanning 6 also changes a relative position of an intersection at which an optical path of the electromagnetic wave transmitting through the second DUT 20 and the second DUT 20 intersect with respect to the second DUT 20. The operation of the stage for scanning 6 is the same as the case in which the (first) DUT 1 and the container 5 are fixed to the stage for scanning 6 (refer to FIGS. 2(*a*), 2(*b*), 3(*a*), 3(*b*), 12(*a*), 12(*b*), 13(*a*), and 13(*b*)).

The phase deriving unit 12, as in the first embodiment, derives a first phase $Ph_1'(x, \theta, f)$, which is the phase in the frequency domain of the electromagnetic wave which has transmitted through the first DUT 1. The phase deriving unit 12 further derives a second phase $Ph_2(x, \theta, f)$ in the frequency domain of the electromagnetic wave (such as a terahertz wave) which has transmitted through the second DUT 20.

The A/D converter 11, the delay period recording unit 13, and the integration unit 17 are the same as those of the first embodiment, and descriptions thereof, therefore, are omitted.

The delay-corrected phase deriving unit 19, as in the first embodiment, subtracts the output (value obtained by integrating the delay period $\Delta t(x, \theta)$ with respect to the frequency f) of the integration unit 17 from the first phase $Ph_1'(x, \theta, f)$ derived by the phase deriving unit 12, thereby deriving the delay-corrected phase $Ph_1(x, \theta, f)$.

The group delay deriving unit 14, as in the first embodiment, receives the delay-corrected phase $Ph_1(x, \theta, f)$ from the delay-corrected phase deriving unit 19, and derives a first group delay $GD_1(x, \theta, f)$ in the frequency domain of the electromagnetic wave which has transmitted through the first DUT 1 based on the delay-corrected phase $Ph_1(x, \theta, f)$. The group delay deriving unit 14 further receives the second phase $Ph_2(x, \theta, f)$, and derives a second group delay $GD_2(x, \theta, f)$ in the frequency domain of the electromagnetic wave which has transmitted through the second DUT 20 based on the second phase $Ph_2(x, \theta, f)$.

The sinogram deriving unit 16 derives a sinogram for a difference in the group delay between the first DUT 1 and the second DUT 20 based on a difference between the first group delay $GD_1(x, \theta, f)$ and the second group delay $GD_2(x, \theta, f)$.

It should be noted that the sinogram $S_{rn}(x, \theta)$ for the difference in the group delay is derived by the sinogram deriving unit 16 according to the following equation (6).

$$S_{rn}(x,\theta)=\int(GD_1(x,\theta,f)-GD_2(x,\theta,f))df \qquad \text{Equation (6)}$$

The tomogram deriving unit 18 derives the image F(x, y) of the cross section of the DUT 1 as in the first embodiment. The image F(x, y) can be derived by replacing S(x, θ) in the equation (5) by the sinogram $S_{rn}(x, \theta)$.

The display 8 shows the image derived by the image deriving device 10.

A description will now be given of an operation of the second embodiment.

First, the second DUT 20 is fixed to the stage for scanning 6 (refer to FIG. 5(*a*)). Then, as in the first embodiment, the scanning of the second DUT 20 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_2(x, \theta, f)$ in the frequency domain of the electromagnetic wave which has transmitted through the second DUT 20. As in the first embodiment, the group delay deriving unit 14 derives, by partially differentiating the phase $Ph_2(x, \theta, f)$ with respect to the frequency f, the second group delay $GD_2(x, \theta, f)$, which is a group delay in the frequency domain of the electromagnetic wave which has transmitted through the second DUT 20.

Then, the first DUT 1 is fixed to the stage for scanning 6 (refer to FIG. 5(*b*)). Then, as in the first embodiment, the scanning of the first DUT 1 is carried out.

The detected result by the electromagnetic wave detector 4 is fed to the A/D converter 11 of the image deriving device 10.

The detected result by the electromagnetic wave detector 4 is converted by the A/D converter 11 into the digital signal, and the digital signal is fed to the phase deriving unit 12.

The phase deriving unit 12 derives the first phase $Ph_1'(x, \theta, f)$ in the frequency domain of the electromagnetic wave which has transmitted through the first DUT 1. As in the first embodiment, the delay-corrected phase deriving unit 19 derives the delay-corrected phase $Ph_1(x, \theta, f)$ by subtracting the output of the integration unit 17 from the first phase $Ph_1'(x, \theta, f)$.

The group delay deriving unit 14 derives, by partially differentiating the delay-corrected phase $Ph_1(x, \theta, f)$ with respect to the frequency f, the first group delay $GD_1(x, \theta, f)$, which is a group delay in the frequency domain of the electromagnetic wave which has transmitted through the first DUT 1.

On this occasion, the sinogram deriving unit 16 receives the first group delay $GD_1(x, \theta, f)$ and the second group delay $GD_2(x, \theta, f)$ from the group delay deriving unit 14, and derives the sinogram $S_{rn}(x, \theta)$ for the difference in the group delay between the first DUT 1 and the second DUT 20 based on the difference between the first group delay $GD_1(x, \theta, f)$ and the second group delay $GD_2(x, \theta, f)$ (refer to an equation (6)).

The tomogram deriving unit 18 derives the image of the cross section of the DUT 1 as in the first embodiment.

The display 8 shows the image derived by the image deriving device 10.

According to the second embodiment, when the CT is carried out for the DUT 1 stored in the container 5 based on the phase $Ph_1'(x, \theta, f)$ and the phase $Ph_2(x, \theta, f)$ (specifically, based on the difference between the first group delay and the second group delay), it is possible to remove the error caused by the delay of the electromagnetic wave as a result of the electromagnetic wave transmitting through the container 5 from the phase $Ph_1'(x, \theta, f)$.

When the refractive index of the second DUT 20 is known (when the second DUT 20 contains air (including nitrogen atmosphere or vacuum), for example), the image can be displayed for the refractive index of the first DUT 1. If the second DUT 20 is the air, it is not necessary to fix the second DUT 20 to the stage for scanning 6, and to move the second DUT 20 in the X direction.

In this case, the sinogram deriving unit 16 derives a sinogram $S_n(x, \theta)$ for the refractive index of the first DUT 1 from the sinogram $S_{rn}(x, \theta)$ for the difference in the group delay according to the following equation (7). It should be noted that c is the velocity of light, and $\Delta x$ is a spatial resolution of the sinogram. Moreover, it is assumed that the refractive index of the second DUT 20 is 1. Further, the sinogram $S_{rn}(x, \theta)$ for the difference in the group delay is derived based on the difference between the first group delay $GD_1(x, \theta, f)$ and the second group delay $GD_2(x, \theta, f)$ as described before.

$$S_n(x,\theta)=1+c(S_{rn}(x,\theta))/\Delta x \quad \text{Equation (7)}$$

The tomogram deriving unit 18 derives an image of the cross section of the DUT 1 from the sinogram $S_n(x, \theta)$ for the refractive index of the first DUT as in the first embodiment (it should be noted that $S_{rn}(x, \theta)$ in the equation (6) is replaced by $S_n(x, \theta)$). The display 8 shows the image derived by the image deriving device 10.

Third Embodiment

Though a third embodiment uses the first DUT 1 and the second DUT 20 as in the second embodiment, the third embodiment is different from the second embodiment in the derivation of a sinogram by the sinogram deriving unit 16, and the derivation of an image by the tomogram deriving unit 18.

Figure 7:
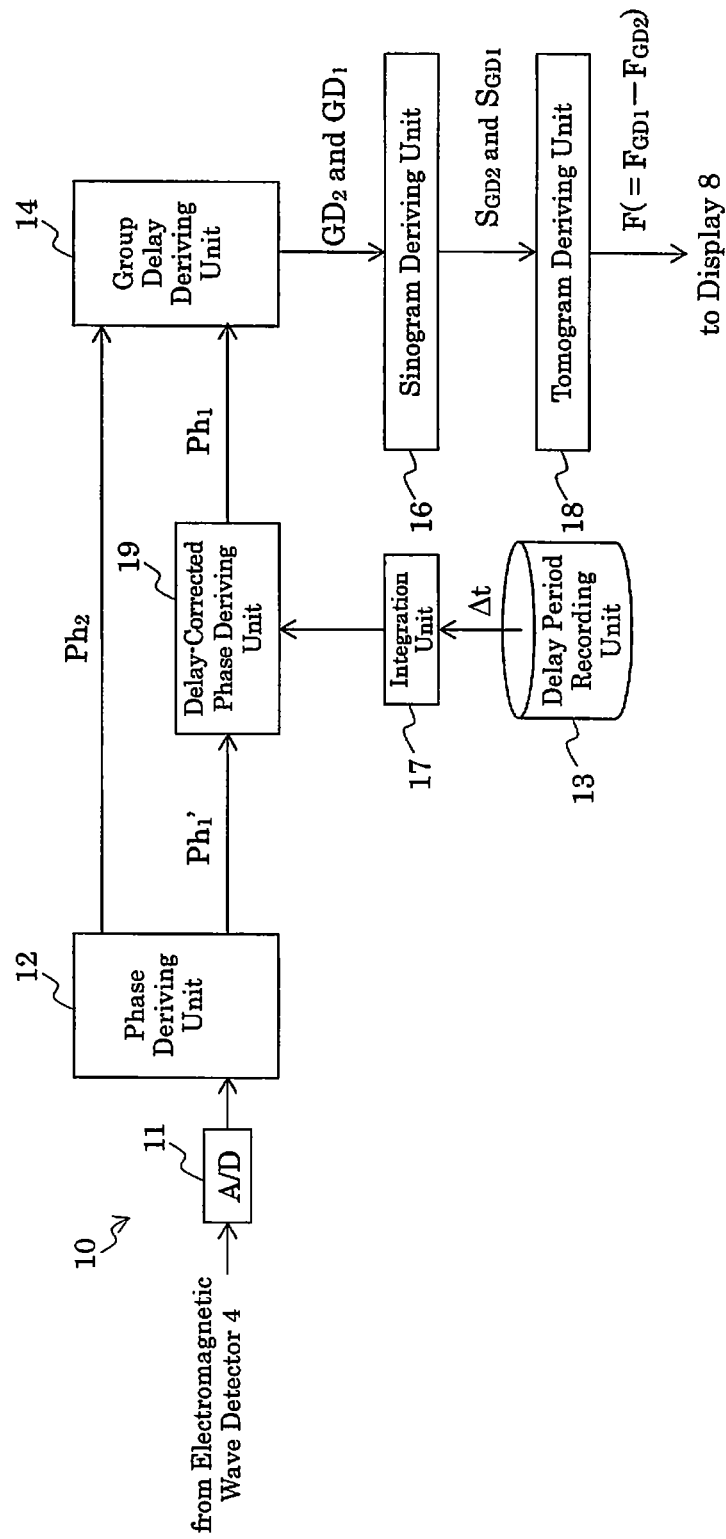
FIG. 7 is a functional block diagram showing a configuration of the image deriving device 10 according to the third embodiment.

FIG. 7 is a functional block diagram showing a configuration of the image deriving device 10 according to the third embodiment.

The configuration of the electromagnetic wave measurement device according to the third embodiment is the same as that of the second embodiment, and hence a description thereof is omitted. Moreover, the image deriving device 10 according to the third embodiment includes the A/D converter 11, the phase deriving unit 12, the delay period recording unit 13, the group delay deriving unit 14, the sinogram deriving unit 16, the integration unit 17, the tomogram deriving unit (image deriving unit) 18, and the delay-corrected phase deriving unit 19. In the following section, the same components are denoted by the same numerals as of the second embodiment, and will be explained in no more details.

The A/D converter 11, the phase deriving unit 12, the delay period recording unit 13, the group delay deriving unit 14, the integration unit 17, and the delay-corrected phase deriving unit 19 are the same as those of the second embodiment, and will be explained in no more details.

The sinogram deriving unit 16 derives a first sinogram $S_{GD1}(x, \theta)$ based on the first group delay $GD_1(x, \theta, f)$ and a second sinogram $S_{GD2}(x, \theta)$ based on the second group delay $GD_2(x, \theta, f)$ (refer to the equation (3), where the second sinogram $S_{GD2}(x, \theta)$ is obtained by replacing $GD_1(x, \theta, f)$ of the equation (3) by $GD_2(x, \theta, f)$).

The tomogram deriving unit (image deriving unit) 18 derives an image $F_{GD1}(x, y)$ of the cross section of the first DUT 1 based on the first sinogram $S_{GD1}(x, \theta)$ and an image $F_{GD2}(x, y)$ of the cross section of the second DUT 20 based on the second sinogram $S_{GD2}(x, \theta)$. It should be noted that the method of deriving the image $F_{GD1}(x,y)$ and the image $F_{GD2}(x,y)$ is the same as that of the first embodiment. In other words, the image $F_{GD1}(x, y)$ and the image $F_{GD2}(x, y)$ can be derived by respectively assigning the first sinogram $S_{GD1}(x, \theta)$ and the second sinogram $S_{GD2}(x, \theta)$ to the sinogram $S(x, \theta)$ in the equation (5).

The tomogram deriving unit 18 further derives the image $F(x, y)$ representing a difference in the group delay between the first DUT 1 and the second DUT 20 as a difference between the image $F_{GD1}(x, y)$ of the cross section of the first DUT 1 and the image $F_{GD2}(x, y)$ of the cross section of the second DUT 20. It should be noted that $F(x, y)=F_{GD1}(x, y)-F_{GD2}(x, y)$. The image $F(x, y)$ represents the difference in the group delay between the first DUT 1 and the second DUT 20 as well as a difference in the refractive index between the first DUT 1 and the second DUT 20.

A description will now be given of an operation of the third embodiment.

The operation up to the derivation of the second group delay $GD_2(x, \theta, f)$ and the first group delay $GD_1(x, \theta, f)$ is the same as that of the second embodiment.

First, the second DUT 20 is fixed to the stage for scanning 6 (refer to FIG. 5(a)). Then, as in the first embodiment, the scanning of the second DUT 20 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_2(x, \theta, f)$ in the frequency domain of the electromagnetic wave which has transmitted through the second DUT 20. As in the first embodiment, the group delay deriving unit 14 derives, by partially differentiating the phase $Ph_2(x, \theta, f)$ with respect to the frequency f, the second group delay $GD_2(x, \theta, f)$, which is a group delay in the frequency domain of the electromagnetic wave which has transmitted through the second DUT 20.

Then, the first DUT 1 is fixed to the stage for scanning 6 (refer to FIG. 5(*b*)). Then, as in the first embodiment, the scanning of the first DUT 1 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the first phase $Ph_1'(x, \theta, f)$ in the frequency domain of the electromagnetic wave which has transmitted through the first DUT 1. As in the first embodiment, the delay-corrected phase deriving unit 19 derives the delay-corrected phase $Ph_1(x, \theta, f)$ by subtracting the output of the integration unit 17 from the first phase $Ph_1'(x, \theta, f)$.

The group delay deriving unit 14 derives, by partially differentiating the delay-corrected phase $Ph_1(x, \theta, f)$ with respect to the frequency f, the first group delay $GD_1(x, \theta, f)$, which is a group delay in the frequency domain of the electromagnetic wave which has transmitted through the first DUT 1.

The operation up to this point is the same as that of the second embodiment.

On this occasion, the sinogram deriving unit 16 receives the first group delay $GD_1(x, \theta, f)$ and the second group delay $GD_2(x, \theta, f)$ from the group delay deriving unit 14, and derives the first sinogram $S_{GD1}(x, \theta)$ based on the first group delay $GD_1(x, \theta, f)$ and the second sinogram $S_{GD2}(x, \theta)$ based on the second group delay $GD_2(x, \theta, f)$.

It should be noted that the first sinogram $S_{GD1}(x, \theta)$ is an integral of the first group delay $GD_1(x, \theta, f)$ with respect to the frequency. The second sinogram $S_{GD2}(x, \theta)$ is an integral of the second group delay $GD_2(x, \theta, f)$ with respect to the frequency.

The tomogram deriving unit 18 derives the image $F_{GD1}(x, y)$ of the cross section of the first DUT 1 based on the first sinogram $S_{GD1}(x, \theta)$ and the image $F_{GD2}(x, y)$ of the cross section of the second DUT 20 based on the second sinogram $S_{GD2}(x, \theta)$.

The tomogram deriving unit 18 further derives the image $F(x, y)$ representing the difference in the group delay between the first DUT 1 and the second DUT 20 as the difference between the image $F_{GD1}(x, y)$ of the cross section of the first DUT 1 and the image $F_{GD2}(x, y)$ of the cross section of the second DUT 20. The display 8 shows the image derived by the image deriving device 10.

According to the third embodiment, when the CT is carried out based on, not an absorption rate of the electromagnetic wave by the DUT 1, but the phase $Ph_1(x, \theta, f)$ and the phase $Ph_2(x, \theta, f)$ (specifically, based on the first group delay and the second group delay), it is possible to remove the error caused by the delay of the electromagnetic wave as a result of the electromagnetic wave transmitting through the container 5 from the phase $Ph_1'(x, \theta, f)$.

Fourth Embodiment

The electromagnetic wave measurement device according to a fourth embodiment is different from that of the first embodiment in that the image deriving device 10 corrects a sinogram for the group delay (or chromatic diffusion) in place of the phase.

Figure 8:
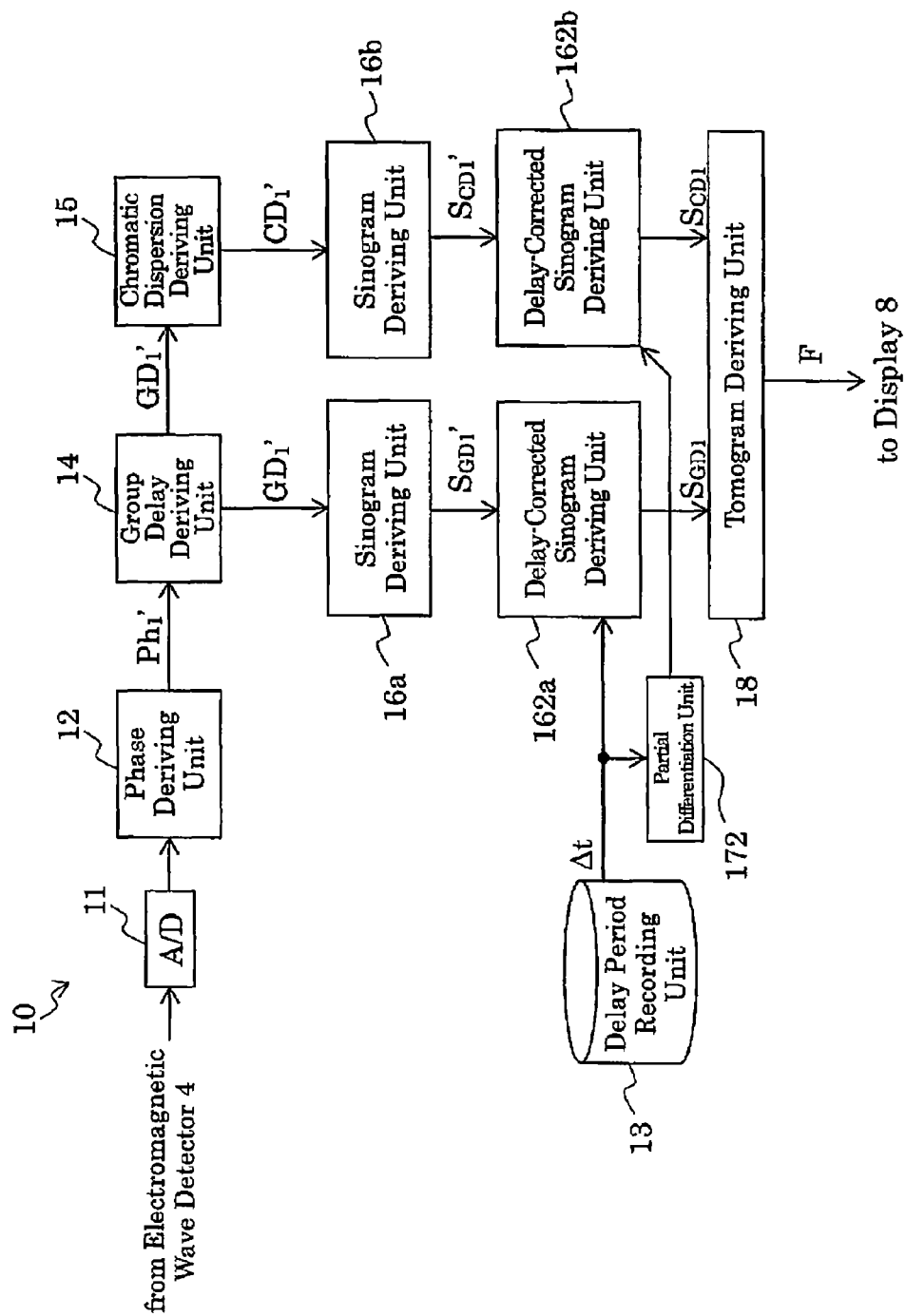
FIG. 8 is a functional block diagram showing a configuration of the image deriving device 10 according to the fourth embodiment.

FIG. 8 is a functional block diagram showing a configuration of the image deriving device 10 according to the fourth embodiment.

The configuration of the electromagnetic wave measurement device according to the fourth embodiment is the same as that of the first embodiment (refer to FIG. 1), and hence a description thereof is omitted. The container 5 is the same as that of the first embodiment, and hence a description thereof is omitted.

Moreover, the image deriving device 10 according to the fourth embodiment includes the A/D converter 11, the phase deriving unit 12, the delay period recording unit 13, the group delay deriving unit 14, the chromatic dispersion deriving unit 15, sinogram deriving units 16*a* and 16*b*, delay-corrected sinogram deriving units 162*a* and 162*b*, a partial differentiation unit 172, and the tomogram deriving unit (image deriving unit) 18. In the following section, the same components are denoted by the same numerals as of the first embodiment, and will be explained in no more details.

The A/D converter 11, the phase deriving unit 12, and the delay period recording unit 13 are the same as those of the first embodiment, and descriptions thereof, therefore, are omitted.

The group delay deriving unit 14 receives the phase $Ph_1'(x, \theta, f)$ from the phase deriving unit 12, and derives a group delay $GD_1'(x, \theta, f)$ in the frequency domain of the electromagnetic wave which has transmitted through the DUT 1 based on the phase $Ph_1'(x, \theta, f)$. The method of deriving the group delay $GD_1'(x, \theta, f)$ is the same as that of the first embodiment. In other words, the group delay $GD_1'(x, \theta, f)$ can be derived by partially differentiating the phase $Ph_1'(x, \theta, f)$ with respect to the frequency f.

The chromatic dispersion deriving unit 15 derives a chromatic dispersion $CD_1'(x, \theta, f)$ in the frequency domain of the electromagnetic wave which has transmitted through the DUT 1 based on a derived result by the phase deriving unit 12. The method of deriving the chromatic dispersion $CD_1'(x, \theta, f)$ is the same as that of the first embodiment.

Specifically, the chromatic dispersion deriving unit 15 receives the group delay $GD_1'(x, \theta, f)$ from the group delay deriving unit 14, and derives the chromatic dispersion $CD_1'(x, \theta, f)$ in the frequency domain of the electromagnetic wave which has transmitted through the DUT 1.

The chromatic dispersion $CD_1'(x, \theta, f)$ can be obtained by partially differentiating the group delay $GD_1'(x, \theta, f)$ with respect to the frequency f.

Moreover, the chromatic dispersion deriving unit 15 may receive the phase $Ph_1'(x, \theta, f)$ from the phase deriving unit 12, and may replace phase $Ph_1(x, \theta, f)$ in the equation (2) by the phase $Ph_1'(x, \theta, f)$, thereby deriving the chromatic dispersion $CD_1'(x, \theta, f)$.

The sinogram deriving unit 16*a* receives the group delay $GD_1'(x, \theta, f)$ from the group delay deriving unit 14, and derives a sinogram $S_{GD1}'(x, \theta)$ based on the group delay $GD_1'(x, \theta, f)$ as in the first embodiment (it should be noted that $GD_1(x, \theta, f)$ in the equation (3) is replaced by $GD_1'(x, \theta, f)$). The sinogram $S_{GD1}'(x, \theta)$ contains an error, namely the delay period $\Delta t(x, \theta)$.

The sinogram deriving unit 16*b* receives the chromatic dispersion $CD_1'(x, \theta, f)$ from the chromatic dispersion deriving unit 15, and derives a sinogram $S_{CD1}'(x, \theta)$ based on the chromatic dispersion $CD_1'(x, \theta, f)$ as in the first embodiment (it should be noted that $CD_1(x, \theta, f)$ in the equation (4) is replaced by $CD_1'(x, \theta, f)$). The sinogram $S_{CD1}'(x, \theta)$ contains an error caused by the delay period $\Delta t(x, \theta)$.

The delay-corrected sinogram deriving unit 162*a* reads the delay period $\Delta t(x, \theta)$ from the delay period recording unit 13, and derives a delay-corrected sinogram $S_{GD1}(x, \theta)$ which is obtained by subtracting the delay period $\Delta t(x, \theta)$ from the sinogram $S_{GD1}'(x, \theta)$. The delay-corrected sinogram $S_{GD1}(x, \theta)$ is a sinogram obtained by subtracting the delay period $\Delta t(x, \theta)$, which is the error, from the sinogram $S_{GD1}'(x, \theta)$.

The partial differentiation unit 172 partially differentiates the delay period $\Delta t(x, \theta)$ with respect to the frequency f.

The delay-corrected sinogram deriving unit 162b derives a delay-corrected sinogram $S_{CD1}(x, \theta)$ which is obtained by subtracting an output (a value obtained by partially differentiating the delay period $\Delta t(x, \theta)$ with respect to the frequency f) of the partial differentiation unit 17 from the sinogram $S_{CD1}'(x, \theta)$. The delay-corrected sinogram $S_{CD1}(x, \theta)$ is a sinogram obtained by subtracting an error caused by the delay period $\Delta t(x, \theta)$ from the sinogram $S_{CD1}'(x, \theta)$.

The tomogram deriving unit (image deriving unit) 18 receives the delay-corrected sinogram $S_{GD1}(x, \theta)$ or $S_{CD1}(x, \theta)$ from the delay-corrected sinogram deriving unit 162a or 162b, and derives an image of the cross section of the DUT 1 including the intersection 100 based on the sinogram as in the first embodiment (refer to the equation (5), $S_{GD1}(x, \theta)$ or $S_{CD1}(x, \theta)$ is assigned to $S(x, \theta)$ of the equation (5)).

A description will now be given of an operation of the fourth embodiment.

First, the DUT 1 is fixed to the stage for scanning 6. Then, while the stage for scanning 6 is moving in the X direction and the Z direction (direction perpendicular to the sheet of FIG. 1) as well as the $\theta$ direction, the electromagnetic wave output device 2 outputs the electromagnetic wave having a frequency equal to or more than 0.01 [THz] and equal to or less than 100 [THz] (such as a terahertz wave) toward the DUT 1. The terahertz wave output toward the DUT 1 transmits through the DUT 1. The electromagnetic wave which has transmitted through the DUT 1 is detected by the electromagnetic wave detector 4. In this way, the DUT 1 is scanned.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_1'(x, \theta, f)$ in the frequency domain of the electromagnetic wave which has transmitted through the DUT 1. The phase $Ph_1'(x, \theta, f)$ contains the error caused by the delay of the electromagnetic wave (such a terahertz wave) which is a result of the electromagnetic wave transmitting though the container 5.

The group delay $GD_1'(x, \theta, f)$ and the chromatic dispersion $CD_1'(x, \theta, f)$ are derived based on the phase $Ph_1'(x, \theta, f)$, and are fed to the sinogram deriving unit 16.

The sinogram deriving unit 16 derives the sinogram $S_{GD1}'(x, \theta)$ based on the group delay, or the sinogram $S_{CD1}'(x, \theta)$ based on the chromatic dispersion. The error is removed from the derived sinogram by the delay-corrected sinogram deriving unit 162a or 162b, resulting in the delay-corrected sinogram $S_{GD1}(x, \theta)$ or $S_{CD1}(x, \theta)$.

The tomogram deriving unit 18 derives the image of the cross section of the DUT 1 based on the delay-corrected sinogram $S_{GD1}(x, \theta)$ or $S_{CD1}(x, \theta)$.

The display 8 shows the image derived by the image deriving device 10.

According to the fourth embodiment, when the CT is carried out for the DUT 1 stored in the container 5 based on the phase $Ph_1'(x, \theta, f)$ (specifically, based on the group delay or the chromatic dispersion), it is possible to remove the error caused by the delay of the electromagnetic wave as a result of the electromagnetic wave transmitting through the container 5 from the sinogram $S_{GD1}'(x, \theta)$ for the group delay and the sinogram $S_{CD1}'(x, \theta)$ for the chromatic dispersion.

As a variation of the fourth embodiment, the group delay $GD_1'(x, \theta, f)$ and the chromatic dispersion $CD_1'(x, \theta, f)$ may be corrected.

Figure 14:
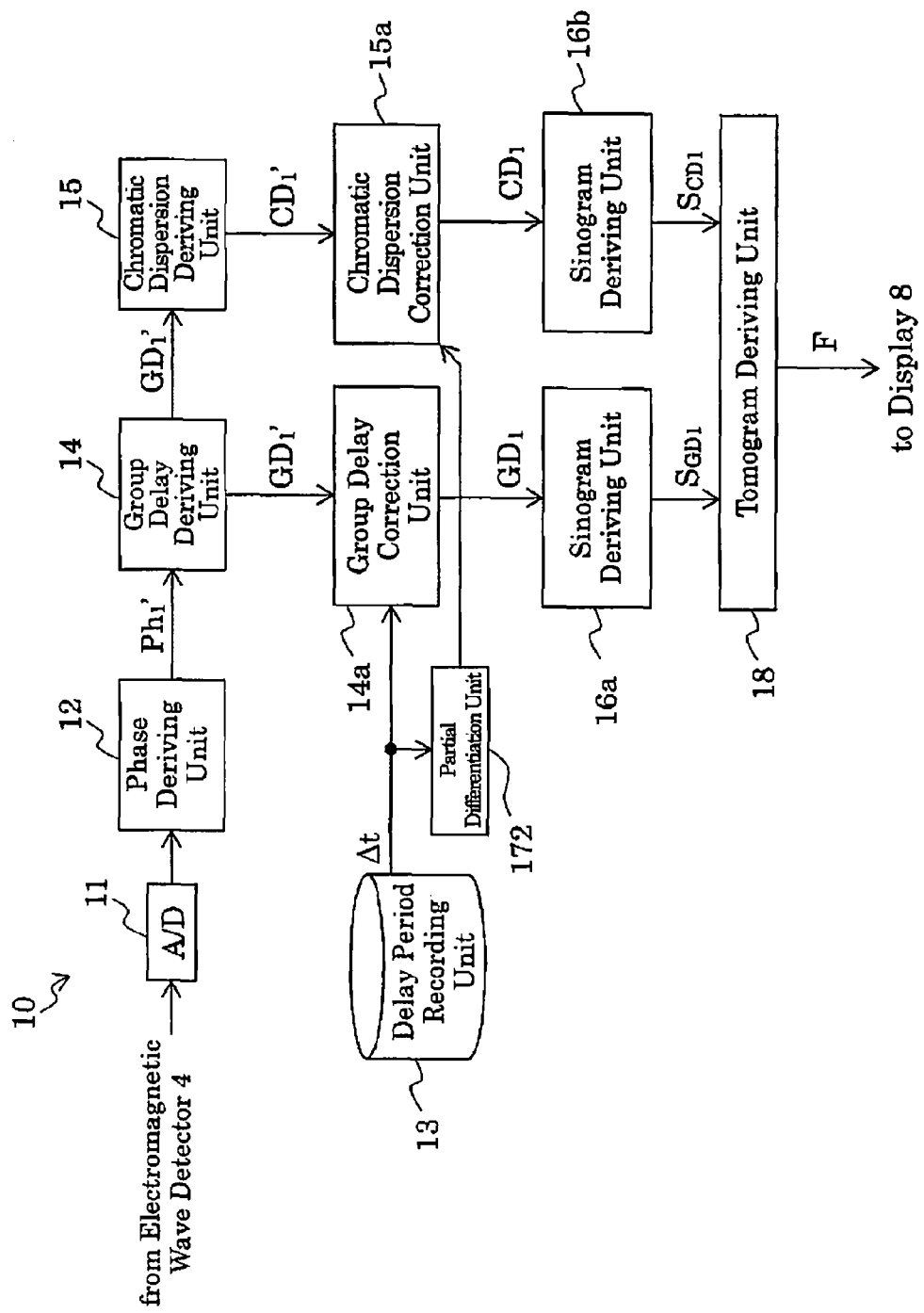
FIG. 14 is a functional block diagram showing a configuration of the image deriving device 10 according to the variation of the fourth embodiment.

FIG. 14 is a functional block diagram showing a configuration of the image deriving device 10 according to the variation of the fourth embodiment. The A/D converter 11, the phase deriving unit 12, the group delay deriving unit 14, the chromatic dispersion deriving unit 15, and the partial differentiation unit 172 in the image deriving device 10 according to the variation of the fourth embodiment are the same as those of the fourth embodiment.

The delay period recording unit 13 records the delay period $\Delta t(x, \theta, f)$ as $\Delta t(x, \theta, f) = \Delta t(x, \theta)$ for all f's in a frequency band in which the phase $Ph_1'(x, \theta, f)$ is derived. In other words, $\Delta t$ is considered as constant regardless of f.

A group delay correction unit 14a derives a corrected group delay which is obtained by subtracting the delay period $\Delta t(x, \theta, f)$ from the group delay $GD_1'(x, \theta, f)$. The corrected group delay is then denoted by $GD_1(x, \theta, f)$.

A chromatic dispersion correction unit 15a derives a corrected chromatic dispersion obtained by subtracting a value obtained by partially differentiating the delay period $\Delta t(x, \theta, f)$ with respect to the frequency f from the chromatic dispersion $CD_1'(x, \theta, f)$. The corrected chromatic dispersion is then denoted by $CD_1(x, \theta, f)$.

The sinogram deriving unit 16a derives the sinogram (which is denoted by $S_{GD1}(x, \theta)$) based on the corrected group delay $GD_1(x, \theta, f)$. The sinogram deriving unit 16b derives the sinogram (which is denoted by $S_{CD1}(x, \theta)$) based on the corrected chromatic dispersion $CD_1(x, \theta, f)$.

The tomogram deriving unit 18 derives the image of the cross section of the DUT 1 based on the sinogram $S_{GD1}(x, \theta)$ or $S_{CD1}(x, \theta)$.

Fifth Embodiment

A fifth embodiment is different from the fourth embodiment in that the (first) DUT 1 and the second DUT 20 are used. The DUT 1 according to the fourth embodiment is referred to as the first DUT 1 according to the fifth embodiment.

Figure 9:
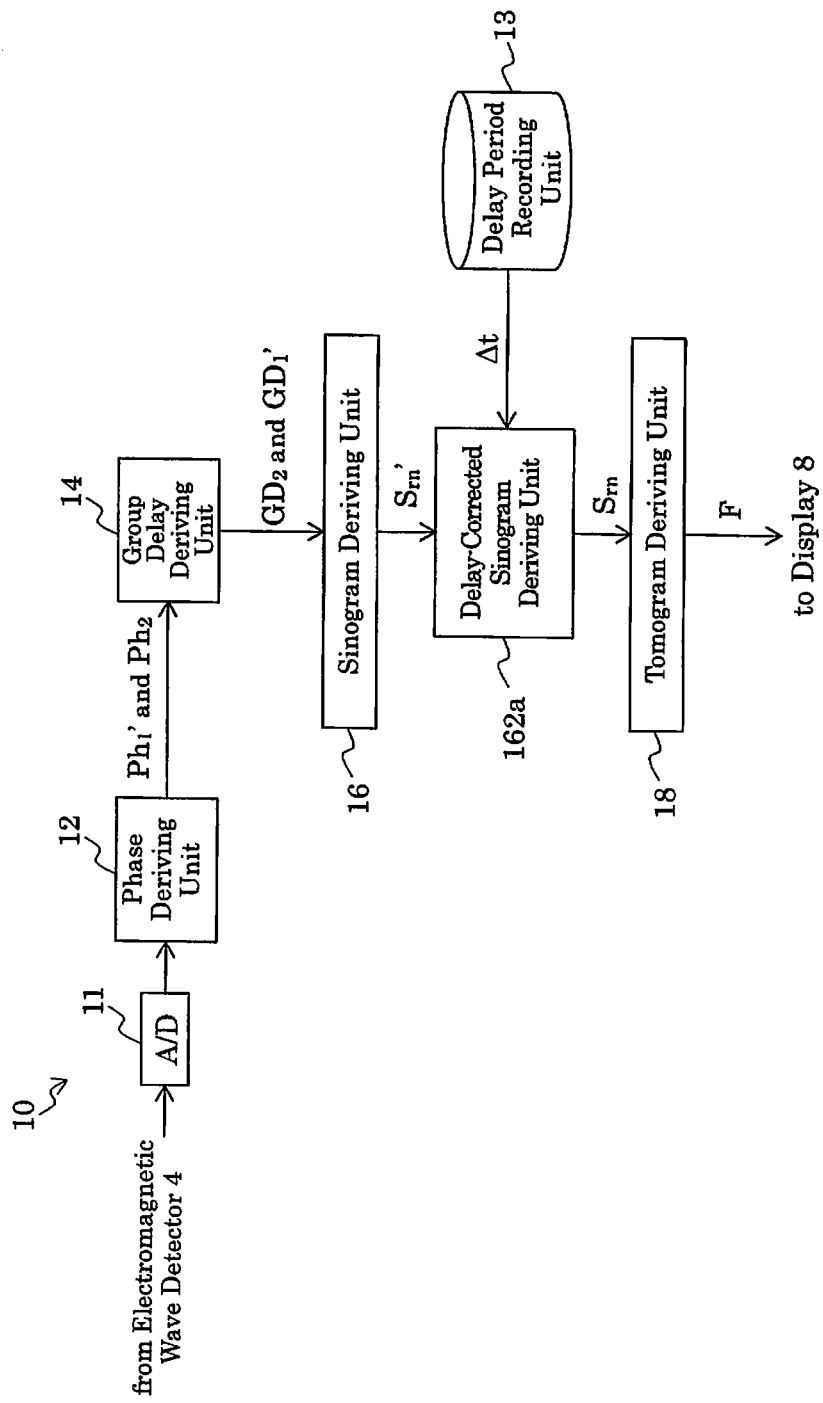
FIG. 9 is a functional block diagram showing a configuration of the image deriving device 10 according to the fifth embodiment.

The configuration of the electromagnetic wave measurement device according to the fifth embodiment is the same as that of the second embodiment, and hence a description thereof is omitted. FIG. 9 is a functional block diagram showing a configuration of the image deriving device 10 according to the fifth embodiment. In the following section, the same components are denoted by the same numerals as of the fourth embodiment, and will be explained in no more details.

The image deriving device 10 according to the fifth embodiment includes the A/D converter 11, the phase deriving unit 12, the delay period recording unit 13, the group delay deriving unit 14, the sinogram deriving unit 16, the delay-corrected sinogram deriving unit 162a, and the tomogram deriving unit (image deriving unit) 18.

The container 5 is the same as that of the first embodiment, and hence a description thereof is omitted. The (first) DUT 1 is the same as the DUT 1 of the first embodiment, and hence a description thereof is omitted.

The second DUT 20 (refer to FIG. 5(a)) is not stored in the container 5.

The electromagnetic wave output device 2, the electromagnetic wave detector 4, and the stage for scanning 6 are the same as those of the second embodiment, and hence descriptions thereof are omitted.

The A/D converter 11, the phase deriving unit 12, and the delay period recording unit 13 are the same as those of the second embodiment, and descriptions thereof, therefore, are omitted.

The group delay deriving unit 14, as in the fourth embodiment, receives the first phase $Ph_1'(x, \theta, f)$ from the phase deriving unit 12, and derives the first group delay $GD_1'(x, \theta, f)$ in the frequency domain of the electromagnetic wave which has transmitted through the first DUT 1 based on the first phase $Ph_1'(x, \theta, f)$. The group delay deriving unit 14 further receives the second phase $Ph_2(x, \theta, f)$ as in the second embodiment, and derives the second group delay $GD_2(x, \theta, f)$ in the frequency domain of the electromagnetic wave which has transmitted through the second DUT 20 based on the second phase $Ph_2(x, \theta, f)$.

The sinogram deriving unit 16 derives a sinogram for a difference in the group delay between the first DUT 1 and the second DUT 20 based on a difference between the first group delay $GD_1'((x, \theta, f)$ and the second group delay $GD_2(x, \theta, f)$.

It should be noted that a sinogram $S_{rn}'(x, \theta)$ for the difference in the group delay is derived by replacing the $GD_1(x, \theta, f)$ of the equation (6) by $GD_1'(x, \theta, f)$.

The delay-corrected sinogram deriving unit 162a reads the delay period $\Delta t(x, \theta)$ from the delay period recording unit 13, and derives a delay-corrected sinogram $S_{rn}(x, \theta)$ which is obtained by subtracting the delay period $\Delta t(x, \theta)$ from the sinogram $S_{rn}'(x, \theta)$. The delay-corrected sinogram $S_{rn}(x, \theta)$ is a sinogram obtained by subtracting the delay period $\Delta t(x, \theta)$, which is the error, from the sinogram $S_{rn}'(x, \theta)$.

The tomogram deriving unit 18 derives the image $F(x, y)$ of the cross section of the DUT 1 as in the first embodiment. The image $F(x, y)$ can be derived by replacing $S(x, \theta)$ in the equation (5) by $S_{rn}(x, \theta)$.

The display 8 shows the image derived by the image deriving device 10.

A description will now be given of an operation of the fifth embodiment.

First, the second DUT 20 is fixed to the stage for scanning 6 (refer to FIG. 5(a)). Then, as in the first embodiment, the scanning of the second DUT 20 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_2(x, \theta, f)$ in the frequency domain of the electromagnetic wave which has transmitted through the second DUT 20. As in the first embodiment, the group delay deriving unit 14 derives, by partially differentiating the phase $Ph_2(x, \theta, f)$ with respect to the frequency f, the second group delay $GD_2(x, \theta, f)$, which is a group delay in the frequency domain of the electromagnetic wave which has transmitted through the second DUT 20.

Then, the first DUT 1 is fixed to the stage for scanning 6 (refer to FIG. 5(b)). Then, as in the first embodiment, the scanning of the first DUT 1 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the first phase $Ph_1'(x, \theta, f)$ in the frequency domain of the electromagnetic wave which has transmitted through the first DUT 1.

The group delay deriving unit 14 derives, by partially differentiating the first phase $Ph_1'(x, \theta, f)$ with respect to the frequency f, the first group delay $GD_1'(x, \theta, f)$ of the electromagnetic wave which has transmitted through the first DUT 1.

On this occasion, the sinogram deriving unit 16 receives the first group delay $GD_1'(x, \theta, f)$ and the second group delay $GD_2(x, \theta, f)$ from the group delay deriving unit 14, and derives the sinogram $S_{rn}'(x, \theta)$ for the difference in the group delay between the first DUT 1 and the second DUT 20 based on a difference between the first group delay $GD_1'(x, \theta, f)$ and the second group delay $GD_2(x, \theta, f)$ (refer to an equation (6), where $GD_1(x, \theta, f)$ is replaced by $GD_1'(x, \theta, f)$).

Further, the delay-corrected sinogram deriving unit 162a derives the delay-corrected sinogram $S_{rn}(x, \theta)$ which is obtained by subtracting the delay period $\Delta t(x, \theta)$ from the sinogram $S_{rn}'(x, \theta)$ for the difference in the group delay. The delay-corrected sinogram $S_{rn}(x, \theta)$ is a sinogram obtained by subtracting the delay period $\Delta t(x, \theta)$, which is the error, from the sinogram $S_{rn}'(x, \theta)$.

The tomogram deriving unit 18 derives an image of the cross section of the DUT 1 as in the first embodiment.

The display 8 shows the image derived by the image deriving device 10.

According to the fifth embodiment, when the CT is carried out for the DUT 1 stored in the container 5 based on the phase $Ph_1'(x, \theta, f)$ and the phase Phe $(x, \theta, f)$ (specifically, based on the difference between the first group delay and the second group delay), it is possible to remove the error caused by the delay of the electromagnetic wave as a result of the electromagnetic wave transmitting through the container 5 from the sinogram $S_{rn}'(x, \theta)$ for the difference in the group delay.

When the refractive index of the second DUT 20 is known (when the second DUT 20 is air (including nitrogen atmosphere or vacuum), for example) as described in the second embodiment, the image can be displayed for the refractive index of the first DUT 1. If the second DUT 20 is the air, it is not necessary to fix the second DUT 20 to the stage for scanning 6, and to move the second DUT 20 in the X direction.

In this case, the sinogram deriving unit 16 derives a sinogram $S_n'(x, \theta)$ for the refractive index of the first DUT 1 from the sinogram $S_{rn}'(x, \theta)$ for the difference in the group delay according to the above-described equation (7) (it should be noted that $S_{rn}(x, \theta)$ is replaced by $S_{rn}'(x, \theta)$). It should be noted that c is the velocity of light, and $\Delta x$ is the spatial resolution of the sinogram. Moreover, it is assumed that the refractive index of the second DUT 20 is 1. Further, the sinogram $S_{rn}'(x, \theta)$ for the difference in the group delay is derived based on the difference between the first group delay $GD_1'(x, \theta, f)$ and the second group delay $GD_2(x, \theta, f)$ as described before.

The tomogram deriving unit 18 derives an image of the cross section of the DUT 1 from the sinogram $S_n(x, \theta)$ for the refractive index of the first DUT 1 (the delay-corrected sinogram deriving unit 162a obtains the sinogram $S_n(x, \theta)$ by subtracting the delay period $\Delta t(x, \theta)$ from the sinogram $S_n'(x, \theta)$) as in the first embodiment. The display 8 shows the image derived by the image deriving device 10.

As a variation of the fifth embodiment, the group delay $GD_1'(x, \theta, f)$ may be corrected.

Figure 15:
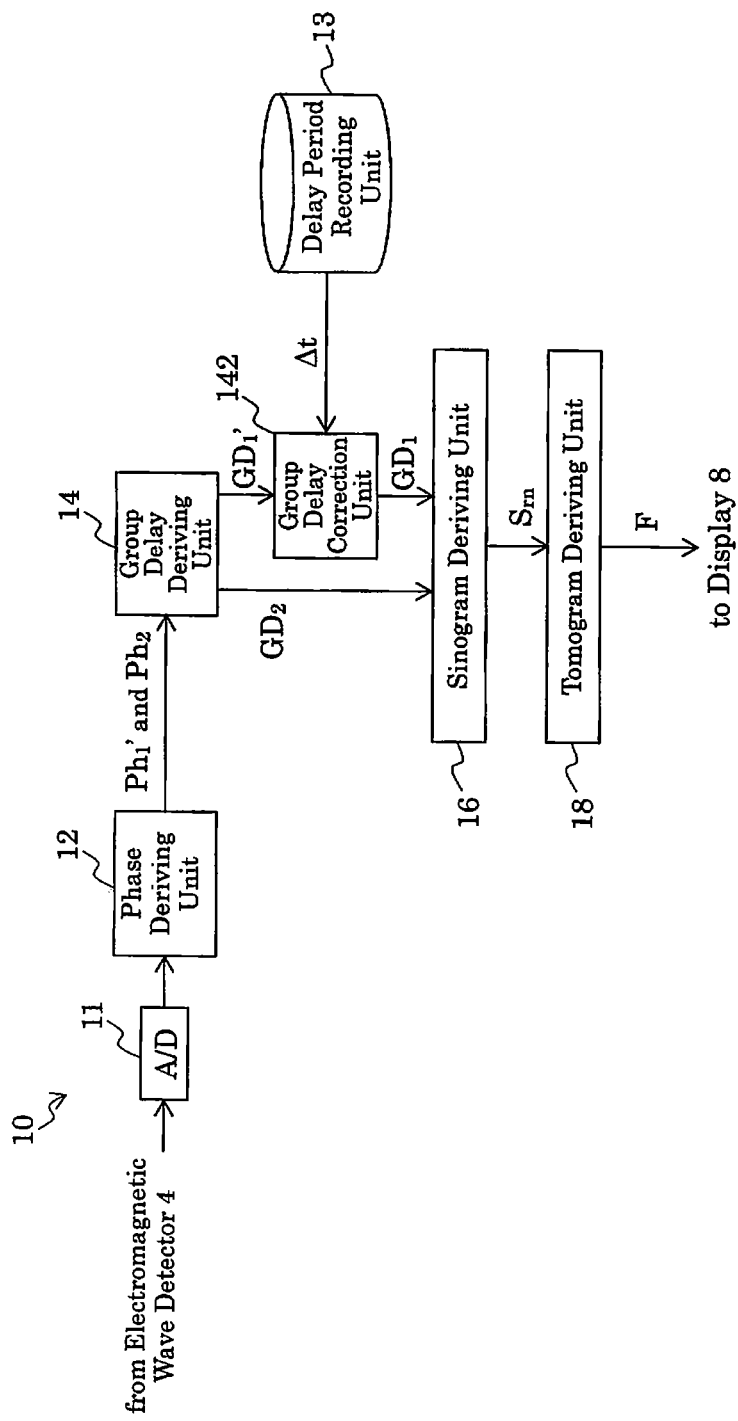
FIG. 15 is a functional block diagram showing a configuration of the image deriving device 10 according to the variation of the fifth embodiment.

FIG. 15 is a functional block diagram showing a configuration of the image deriving device 10 according to the variation of the fifth embodiment. The A/D converter 11, the phase deriving unit 12, and the group delay deriving unit 14 in the image deriving device 10 according to the variation of the fifth embodiment are the same as those of the fifth embodiment.

The delay period recording unit 13 records delay periods $\Delta t(x, \theta, f)$ as $\Delta t(x, \theta, f) = \Delta t(x, \theta)$ for all f's in a frequency band in which the phase $Ph_1'(x, \theta, f)$ is derived. In other words, $\Delta t$ is considered as constant regardless of f.

A group delay correction unit 142 derives a corrected group delay which is obtained by subtracting the delay period $\Delta t(x, \theta, f)$ from the first group delay $GD_1'(x, \theta, f)$. The corrected group delay is then denoted by $GD_1(x, \theta, f)$.

The sinogram deriving unit 16 derives the sinogram (which is denoted by $S_{rn}(x, \theta)$) based on a difference between the corrected group delay $GD_1((x, \theta, f)$ and the second group delay $GD_2(x, \theta, f)$ (refer to the equation (6)).

The tomogram deriving unit 18 derives the image of the cross section of the DUT 1 based on the sinogram $S_{rn}(x, \theta)$.

When the refractive index of the second DUT 20 is known (when the second DUT 20 is air (including nitrogen atmosphere or vacuum), for example), the image can also be displayed for the refractive index of the first DUT 1 as described before.

Sixth Embodiment

Though a sixth embodiment uses the first DUT 1 and the second DUT 20 as in the fifth embodiment, it is different from the fifth embodiment in the derivation of a sinogram by the sinogram deriving unit 16, and the derivation of an image by the tomogram deriving unit 18.

Figure 10:
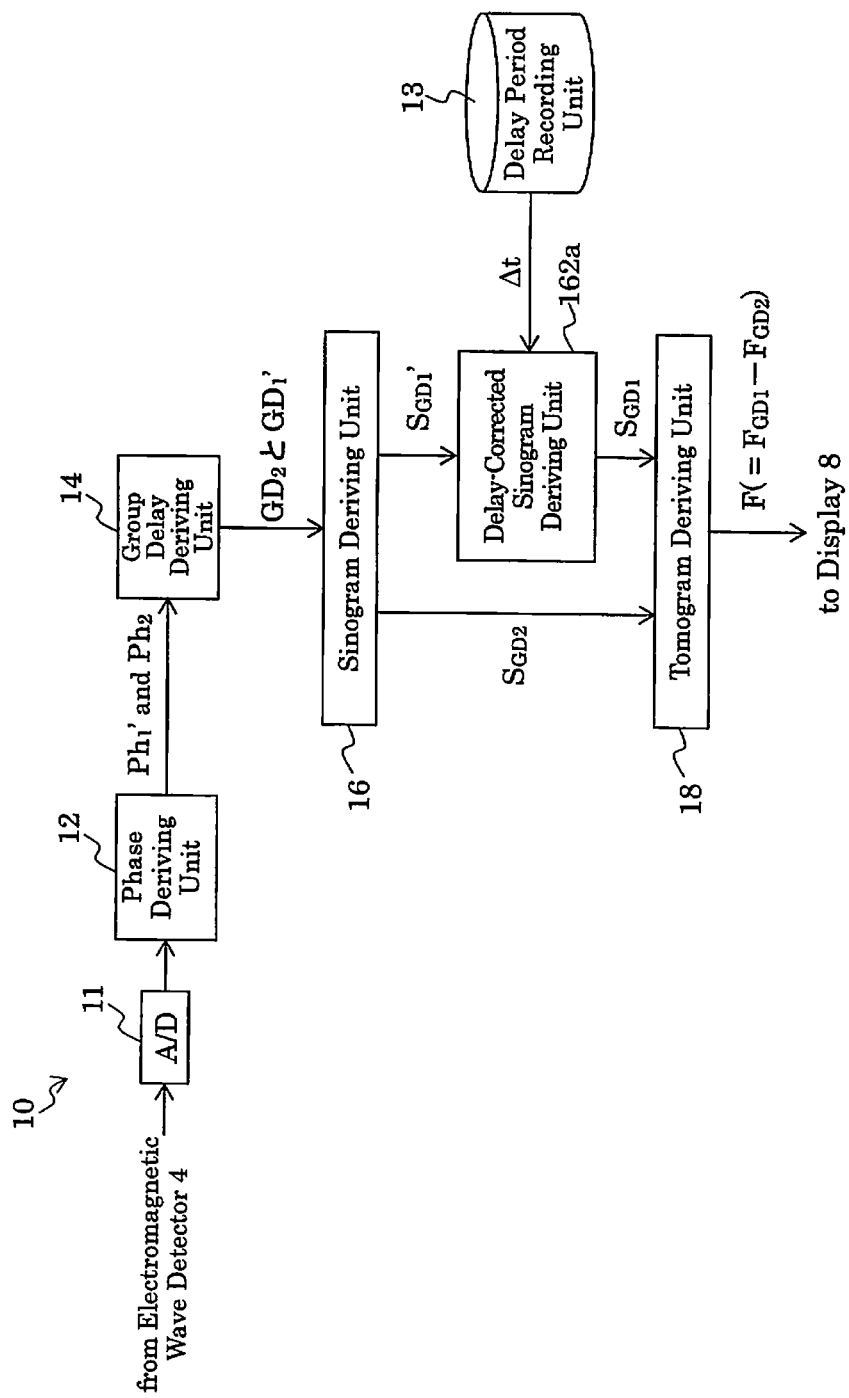
FIG. 10 is a functional block diagram showing a configuration of the image deriving device 10 according to the sixth embodiment.

FIG. 10 is a functional block diagram showing a configuration of the image deriving device 10 according to the sixth embodiment.

The configuration of the electromagnetic wave measurement device according to the sixth embodiment is the same as that of the fifth embodiment, and hence a description thereof is omitted. Moreover, the image deriving device 10 according to the sixth embodiment includes the A/D converter 11, the phase deriving unit 12, the delay period recording unit 13, the group delay deriving unit 14, the sinogram deriving unit 16, the delay-corrected sinogram deriving unit 162a, and the tomogram deriving unit (image deriving unit) 18. In the following section, the same components are denoted by the same numerals as of the fifth embodiment, and will be explained in no more details.

The A/D converter 11, the phase deriving unit 12, the delay period recording unit 13, and the group delay deriving unit 14 are the same as those of the fifth embodiment, and descriptions thereof, therefore, are omitted.

The sinogram deriving unit 16 derives a first sinogram $S_{GD1}'(x, \theta)$ based on the first group delay $GD_1'(x, \theta, f)$ and a second sinogram $S_{GD2}(x, \theta)$ based on the second group delay $GD_2(x, \theta, f)$ (refer to the equation (3), where $GD_1'(x, \theta, f)$ or $GD_2(x, \theta, f)$ is assigned to $GD_1(x, \theta, f)$).

The delay-corrected sinogram deriving unit 162a reads the delay period $\Delta t(x, \theta)$ from the delay period recording unit 13, and derives the delay-corrected sinogram $S_{GD1}(x, \theta)$ which is obtained by subtracting the delay period $\Delta t(x, \theta)$ from the first sinogram $S_{GD1}'(x, \theta)$. The delay-corrected sinogram $S_{GD1}(x, \theta)$ is a sinogram obtained by subtracting the delay period $\Delta t(x, \theta)$, which is the error, from the first sinogram $S_{GD1}'(x, \theta)$.

The tomogram deriving unit (image deriving unit) 18 derives the image $F_{GD1}(x, y)$ of the cross section of the first DUT 1 based on the delay-corrected sinogram $S_{GD1}(x, \theta)$ and the image $F_{GD2}(x, y)$ of the cross section of the second DUT 20 based on the second sinogram $S_{GD2}(x, \theta)$. It should be noted that the method of deriving the image $F_{GD1}(x, y)$ and the image $F_{GD2}(x, y)$ is the same as that of the first embodiment. In other words, the image $F_{GD1}(x, y)$ and the image $F_{GD2}(x, y)$ can be derived by respectively assigning the delay-corrected sinogram $S_{GD1}(x, \theta)$ and the second sinogram $S_{GD2}(x, \theta)$ to the sinogram $S(x, \theta)$ in the equation (5).

The tomogram deriving unit 18 further derives the image $F(x, y)$ representing the difference in the group delay between the first DUT 1 and the second DUT 20 as the difference between the image $F_{GD1}(x, y)$ of the cross section of the first DUT 1 and the image $F_{GD2}(x, y)$ of the cross section of the second DUT 20. It should be noted that $F(x, y) = F_{GD1}(x, y) - F_{GD2}(x, y)$. The image $F(x, y)$ represents the difference in the group delay between the first DUT 1 and the second DUT 20 as well as a difference in the refractive index between the first DUT 1 and the second DUT 20.

The display 8 shows the image derived by the image deriving device 10.

A description will now be given of an operation of the six embodiment.

The operation up to the derivation of the second group delay $GD_2(x, \theta, f)$ and the first group delay $GD_1(x, \theta, f)$ is the same as that of the fifth embodiment.

First, the second DUT 20 is fixed to the stage for scanning 6 (refer to FIG. 5(a)). Then, as in the first embodiment, the scanning of the second DUT 20 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the phase $Ph_2(x, \theta, f)$ in the frequency domain of the electromagnetic wave which has transmitted through the second DUT 20. As in the first embodiment, the group delay deriving unit 14 derives, by partially differentiating the phase $Ph_2(x, \theta, f)$ with respect to the frequency f, the second group delay $GD_2(x, \theta, f)$, which is a group delay in the frequency domain of the electromagnetic wave which has transmitted through the second DUT 20.

Then, the first DUT 1 is fixed to the stage for scanning 6 (refer to FIG. 5(b)). Then, as in the first embodiment, the scanning of the first DUT 1 is carried out.

The detected result by the electromagnetic wave detector 4 is fed to the A/D converter 11 of the image deriving device 10. The detected result by the electromagnetic wave detector 4 is converted by the A/D converter 11 into the digital signal, and the digital signal is fed to the phase deriving unit 12.

The phase deriving unit 12 derives the first phase $Ph_1'(x, \theta, f)$ in the frequency domain of the electromagnetic wave which has transmitted through the first DUT 1.

The group delay deriving unit 14 derives, by partially differentiating the delay-corrected phase $Ph_1(x, \theta, f)$ with respect to the frequency f, the first group delay $GD_1'(x, \theta, f)$, which is a group delay in the frequency domain of the electromagnetic wave which has transmitted through the first DUT 1.

The operation up to this point is the same as that of the fifth embodiment.

On this occasion, the sinogram deriving unit 16 receives the first group delay $GD_1'(x, \theta, f)$ and the second group delay $GD_2(x, \theta, f)$ from the group delay deriving unit 14, and derives the first sinogram $S_{GD1}'(x, \theta)$ based on the first group delay $GD_1'(x, \theta, f)$ and the second sinogram $S_{GD2}(x, \theta)$ based on the second group delay $GD_2(x, \theta, f)$.

It should be noted that the first sinogram $S_{GD1}'(x, \theta)$ is an integral of the first group delay $GD_1(x, \theta, f)$ with respect to the frequency. The second sinogram $S_{GD2}(x, \theta)$ is an integral of the second group delay $GD_2(x, \theta, f)$ with respect to the frequency.

Further, the delay-corrected sinogram deriving unit 162a derives the delay-corrected sinogram $S_{GD1}(x, \theta)$ which is obtained by subtracting the delay period Δt(x, θ) from the first sinogram $S_{GD1}'$(x, θ). The delay-corrected sinogram $S_{GD1}$(x, θ) is a sinogram obtained by subtracting the delay period Δt(x, θ), which is the error, from the first sinogram $S_{GD1}'$(x, θ).

The tomogram deriving unit 18 derives the image $F_{GD1}$(x, y) of the cross section of the first DUT 1 based on the delay-corrected sinogram $S_{GD1}$(x, θ) and the image $F_{GD2}$(x, y) of the cross section of the second DUT 20 based on the second sinogram $S_{GD2}$(x, θ).

The tomogram deriving unit 18 further derives the image F(x, y) representing the difference in the group delay between the first DUT 1 and the second DUT 20 as the difference between the image $F_{GD1}$(x, y) of the cross section of the first DUT 1 and the image $F_{GD2}$(x, y) of the cross section of the second DUT 20. The display 8 shows the image derived by the image deriving device 10.

According to the sixth embodiment, when the CT is carried out based on, not an absorption rate of the electromagnetic wave by the DUT 1, but the phase $Ph_1'$(x, θ, f) and the phase $Ph_2$(x, θ, f) (specifically, based on the first group delay and the second group delay), it is possible to remove the error caused by the delay of the electromagnetic wave as a result of the electromagnetic wave transmitting through the container 5 from the first sinogram $S_{GD1}'$(x, θ).

Seventh Embodiment

The electromagnetic wave measurement device according to a seventh embodiment measures the DUT 1 based on the attenuation ratio of the electromagnetic wave of the DUT 1.

The configuration of the electromagnetic wave measurement device according to the seventh embodiment is the same as that of the first embodiment (refer to FIG. 1), and hence a description thereof is omitted. The container 5 is the same as that of the first embodiment, and hence a description thereof is omitted.

Figure 11:
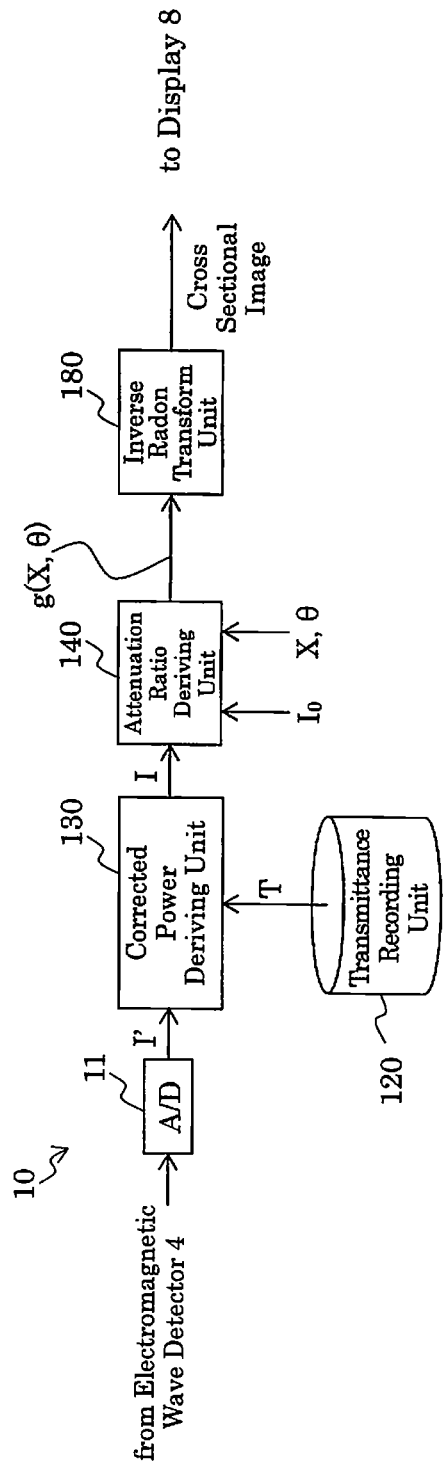
FIG. 11 is a functional block diagram showing a configuration of the image deriving device 10 according to the seventh embodiment.

FIG. 11 is a functional block diagram showing a configuration of the image deriving device 10 according to the seventh embodiment. The image deriving device 10 according to the seventh embodiment includes the A/D converter 11, a transmittance recording unit 120, a corrected power deriving unit 130, an attenuation ratio deriving unit 140, and an inverse radon transform unit 180.

The A/D converter 11 is the same as that of the first embodiment, and a description thereof, therefore, is omitted.

The transmittance recording unit 120 records a value representing a transmittance T at which the power of the electromagnetic wave transmits through the container 5 when a reflection of the electromagnetic wave on transmission surfaces (a first curved surface portion S1 and a second curved surface portion S2) through which the electromagnetic wave transmits in the container 5 is considered. It should be noted that "a value representing a transmittance" may be the transmittance itself, a function of the transmittance (such as a logarithm of the transmittance), or a reflectance (100%−(transmittance)). On this occasion, the transmittance recording unit 120 records the transmittance T itself.

It is assumed that light which has traveled in a medium having a refractive index no is made incident to a medium having a refractive index $n_1$ at an incident angle of $θ_{in1}$. On this occasion, a power reflectance $R_{p1}$ of a p-polarized light is represented by an equation (8), and a power reflectance $R_{s1}$ of an s-polarized light is represented by an equation (9).

$$R_{p1} = \left[ \frac{\left(\frac{n_1}{n_0}\right)^2 \cos θ_{in1} - \sqrt{\left(\frac{n_1}{n_0}\right)^2 - \sin^2 θ_{in1}}}{\left(\frac{n_1}{n_0}\right)^2 \cos θ_{in1} + \sqrt{\left(\frac{n_1}{n_0}\right)^2 - \sin^2 θ_{in1}}} \right]^2 \quad \text{Equation (8)}$$

$$R_{s1} = \left[ \frac{\cos θ_{in1} - \sqrt{\left(\frac{n_1}{n_0}\right)^2 - \sin^2 θ_{in1}}}{\cos θ_{in1} + \sqrt{\left(\frac{n_1}{n_0}\right)^2 - \sin^2 θ_{in1}}} \right]^2 \quad \text{Equation (9)}$$

Thus, it is possible to obtain the power reflectance of the p-polarized light (s-polarized light) at points m, m', n, and n' according to the equations (8) and (9).

On this occasion, the power reflectance of the p-polarized light (s-polarized light) at the point m is denoted by $R_{pm}$ ($R_{sm}$); the power reflectance of the p-polarized light (s-polarized light) at the point m', $R_{pm}'$ ($R_{sm}'$); the power reflectance of the p-polarized light (s-polarized light) at the point n, $R_{pn}$ ($R_{sn}$); and the power reflectance of the p-polarized light (s-polarized light) at the point n', $R_{pn}'$ ($R_{sn}'$).

Then, when the electromagnetic wave (such as a terahertz wave) is the p-polarized light, and a transmittance T is denoted by Tp, Tp is represented by:

$$Tp = (1-R_{pm}')(1-R_{pm})(1-R_{pn})(1-R_{pn}')$$

When the electromagnetic wave (such as a terahertz wave) is the s-polarized light, and a transmittance T is denoted by Ts, Ts is represented by:

$$Ts = (1-R_{sm}')(1-R_{sm})(1-R_{sn})(1-R_{sn}')$$

When the electromagnetic wave is an elliptically polarized light, and contains a p-direction component and an s-direction component at a power ratio a:1−a (0<a<1), the transmittance T is represented by:

$$T = aTp + (1-a)Ts$$

The corrected power deriving unit 130 derives, based on a power (denoted by I'(X, θ)) of the electromagnetic wave detected by the electromagnetic wave detector 4 and the transmittance T, a corrected power I(X, θ), which is a power of the electromagnetic wave detected when the transmittance T is 100%. It should be noted that X is an X-axis intercept of an intersection 100. In other words, X denotes an X-axis coordinate of the intersection point between the X axis (axis extending in the X direction) and the intersection 100. Moreover, θ denotes an angle between the intersection 100 and a horizontal axis orthogonal to the X axis.

The corrected power deriving unit 130 derives a corrected power I as I=I'/T, for example.

The attenuation ratio deriving unit 140 derives an attenuation ratio g(X, θ) of the electromagnetic wave which has transmitted through the DUT 1 based on the corrected power I(X, θ).

A power (intensity) of the electromagnetic wave traveling toward the DUT 1 is denoted by $I_0$. The attenuation ratio g(X, θ) of the electromagnetic wave is then represented as ln($I_0$/I(X, θ)).

The inverse radon transform unit 180 receives the attenuation ratio g(X, θ) from the attenuation ratio deriving unit 140, and carries out an inverse radon transform, thereby acquiring a cross sectional image. The cross sectional image is fed to the display 8. It should be noted that the inverse radon transform unit 18 may determine predetermined colors to be associated with the cross sectional image, and may provide the determined colors to the display 8.

A description will now be given of an operation of the seventh embodiment.

First, the DUT 1 is fixed to the stage for scanning 6. Then, while the stage for scanning 6 is moving in the X direction and the Z direction (direction perpendicular to the sheet of FIG. 1) as well as the θ direction, the electromagnetic wave output device 2 outputs the electromagnetic wave having a frequency equal to or more than 0.01 [THz] and equal to or less than 100 [THz] (such as a terahertz wave) toward the DUT 1. The terahertz wave output toward the DUT 1 transmits through the DUT 1. The electromagnetic wave which has transmitted through the DUT 1 is detected by the electromagnetic wave detector 4. In this way, the DUT 1 is scanned.

The detected result (power I'(X, θ)) by the electromagnetic wave detector 4 is fed to the A/D converter 11 of the image deriving device 10. The detected result by the electromagnetic wave detector 4 is converted by the A/D converter 11 into the digital signal, and the digital signal is fed to the corrected power deriving unit 130. The power I'(X, θ) contains an error caused by the reflection by the container 5.

The corrected power deriving unit 130 derives the corrected power I(X, θ) by dividing the power I'(X, θ) by the transmittance T at which the power of the electromagnetic wave transmits through the container 5. As a result, the error caused by the reflection by the container 5 is removed from the power I', resulting in the corrected power I.

The attenuation ratio deriving unit 140 derives the attenuation ratio g(X, θ)(=ln(I$_0$/I(X, θ))) from the corrected power I(X, θ).

The inverse radon transform unit 180 receives the attenuation ratio g(X, θ) from the attenuation ratio deriving unit 140, and carries out an inverse radon transform, thereby acquiring a cross sectional image.

The cross sectional image is fed to the display 8, and is displayed.

According to the seventh embodiment, when the CT based on the power I'(X, θ) is applied to the DUT 1 stored in the container 5, the error caused by the reflection by the container 5 can be removed from the power I'(X, θ).

Moreover, the above-described embodiments may be realized in the following manner. A computer is provided with a CPU, a hard disk, and a media (such as a floppy disk (registered trade mark) and a CD-ROM) reader, and the media reader is caused to read a medium recording a program realizing the above-described respective components such as the image deriving device 10, thereby installing the program on the hard disk. This method may also realize the above-described functions.

The invention claimed is:

1. An electromagnetic wave measurement device comprising:
    an electromagnetic wave outputter that outputs an electromagnetic wave having a frequency equal to or more than 0.01 THz and equal to or less than 100 THz toward a device under test and a container storing at least a part of the device under test;
    an electromagnetic wave detector that detects the electromagnetic wave which has transmitted through the device under test;
    a relative position changer that changes a relative position of an intersection at which an optical path of the electromagnetic wave transmitting through the device under test and the device under test intersect with respect to the device under test;
    a delay period recorder that records a delay period of the electromagnetic wave caused by a transmission of the electromagnetic wave through the container;
    a phase deriver that derives, based on a detected result by the electromagnetic wave detector, a phase in the frequency domain of the electromagnetic wave which has transmitted through the device under test;
    a delay-corrected phase deriver that derives a delay-corrected phase obtained by subtracting an integral of the delay period with respect to the frequency from the phase;
    a sinogram deriver that derives a sinogram based on a derived result by the delay-corrected phase deriving unit deriver; and
    an image deriver that derives, based on the sinogram, an image of a cross section of the device under test including the intersection.

2. The electromagnetic wave measurement device according to claim 1, comprising a group delay deriver that derives, based on the derived result by the delay-corrected phase deriver, a group delay in the frequency domain of the electromagnetic wave which has transmitted through the device under test, wherein the sinogram deriver derives a sinogram for the group delay.

3. The electromagnetic wave measurement device according to claim 1, comprising a chromatic dispersion deriver that derives, based on the derived result by the delay-corrected phase deriver, a chromatic dispersion in the frequency domain of the electromagnetic wave which has transmitted through the device under test, wherein the sinogram deriver derives a sinogram for the chromatic dispersion.

4. An electromagnetic wave measurement device comprising:
    an electromagnetic wave outputter that outputs an electromagnetic wave having a frequency equal to or more than 0.01 THz and equal to or less than 100 THz toward a first device under test and a container storing at least a part of the first device under test, and further outputs the electromagnetic wave toward a second device under test;
    an electromagnetic wave detector that detects the electromagnetic wave which has transmitted through the first device under test and the electromagnetic wave which has transmitted through the second device under test;
    a relative position changer that changes a relative position of a first intersection at which an optical path of the electromagnetic wave transmitting through the first device under test and the first device under test intersect with respect to the first device under test;
    a delay period recorder that records a delay period of the electromagnetic wave caused by a transmission of the electromagnetic wave through the container;
    a phase deriver that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test;
    a delay-corrected phase deriver that derives a delay-corrected phase obtained by subtracting an integral of the delay period with respect to the frequency from the first phase;
    a group delay deriver that derives, based on a derived result by the delay-corrected phase deriver and the second phase, a first group delay in the frequency domain of the electromagnetic wave which has transmitted through the first device under test, and a second group delay in the frequency domain of the electromagnetic wave which has transmitted through the second device under test;

a sinogram deriver that derives, based on a difference between the first group delay and the second group delay, a sinogram for a difference in the group delay between the first device under test and the second device under test; and an image deriver that derives, based on the sinogram, an image of a cross section of the device under test including the intersection.

5. The electromagnetic wave measurement device according to claim 4, wherein:

the refractive index of the second device under test is known; and the sinogram deriver derives a sinogram for the refractive index of the first device under test based on the difference between the first group delay and the second group delay.

6. An electromagnetic wave measurement device comprising:

an electromagnetic wave outputter that outputs an electromagnetic wave having a frequency equal to or more than 0.01 THz and equal to or less than 100 THz toward a first device under test and a container storing at least a part of the first device under test, and further outputs the electromagnetic wave toward a second device under test;

an electromagnetic wave detector that detects the electromagnetic wave which has transmitted through the first device under test and the electromagnetic wave which has transmitted through the second device under test;

a relative position changer that changes a relative position of a first intersection at which an optical path of the electromagnetic wave transmitting through the first device under test and the first device under test intersect with respect to the first device under test;

a delay period recorder that records a delay period of the electromagnetic wave caused by a transmission of the electromagnetic wave through the container;

a phase deriver that derives, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test;

a delay-corrected phase deriver that derives a delay-corrected phase obtained by subtracting an integral of the delay period with respect to the frequency from the first phase;

a group delay deriver that derives, based on a derived result by the delay-corrected phase deriver and the second phase, a first group delay in the frequency domain of the electromagnetic wave which has transmitted through the first device under test, and a second group delay in the frequency domain of the electromagnetic wave which has transmitted through the second device under test;

a sinogram deriver that derives a first sinogram based on the first group delay, and a second sinogram based on the second group delay; and an image deriver that derives an image of a cross section of the first device under test based on the first sinogram, and an image of a cross section of the second device under test based on the second sinogram, and, as a difference between the image of the cross section of the first device under test and the image of the cross section of the second device under test, derives an image representing a difference in the group delay between the first device under test and the second device under test.

7. A measurement method using an electromagnetic wave measurement device having an electromagnetic wave outputter that outputs an electromagnetic wave having a frequency equal to or more than 0.01 THz and equal to or less than 100 THz toward a device under test and a container storing at least a part of the device under test; an electromagnetic wave detector that detects the electromagnetic wave which has transmitted through the device under test; and a relative position changer that changes a relative position of an intersection at which an optical path of the electromagnetic wave transmitting through the device under test and the device under test intersect with respect to the device under test, the method comprising:

recording a delay period of the electromagnetic wave caused by a transmission of the electromagnetic wave through the container;

deriving, based on a detected result by the electromagnetic wave detector, a phase in the frequency domain of the electromagnetic wave which has transmitted through the device under test;

deriving a delay-corrected phase obtained by subtracting an integral of the delay period with respect to the frequency from the phase;

deriving a sinogram based on a derived result by the deriving of the delay-corrected phase; and deriving, based on the sinogram, an image of a cross section of the device under test including the intersection.

8. A measurement method using an electromagnetic wave measurement device having an electromagnetic wave outputter that outputs an electromagnetic wave having a frequency equal to or more than 0.01 THz and equal to or less than 100 THz toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changer that changes a relative position of a first intersection at which an optical path of the electromagnetic wave transmitting through the first device under test and the first device under test intersect with respect to the first device under test, the method comprising:

recording a delay period of the electromagnetic wave caused by a transmission of the electromagnetic wave through the container;

deriving, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test;

deriving a delay-corrected phase obtained by subtracting an integral of the delay period with respect to the frequency from the first phase;

deriving, based on a derived result by the deriving of the delay-corrected phase and the second phase, a first group delay in the frequency domain of the electromagnetic wave which has transmitted through the first device under test, and a second group delay in the frequency domain of the electromagnetic wave which has transmitted through the second device under test;

deriving, based on a difference between the first group delay and the second group delay, a sinogram for a difference in the group delay between the first device under test and the second device under test; and deriving, based on the sinogram, an image of a cross section of the device under test including the intersection.

9. A measurement method using an electromagnetic wave measurement device having an electromagnetic wave outputter that outputs an electromagnetic wave having a frequency equal to or more than 0.01 THz and equal to or less than 100 THz toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changer that changes a relative position of a first intersection at which an optical path of the electromagnetic wave transmitting through the first device under test and the first device under test intersect with respect to the first device under test, the method comprising:

recording a delay period of the electromagnetic wave caused by a transmission of the electromagnetic wave through the container;

deriving, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test;

deriving a delay-corrected phase obtained by subtracting an integral of the delay period with respect to the frequency from the first phase;

deriving, based on a derived result by the deriving of the delay-corrected phase and the second phase, a first group delay in the frequency domain of the electromagnetic wave which has transmitted through the first device under test, and a second group delay in the frequency domain of the electromagnetic wave which has transmitted through the second device under test;

deriving a first sinogram based on the first group delay, and a second sinogram based on the second group delay; and deriving an image of a cross section of the first device under test based on the first sinogram, and an image of a cross section of the second device under test based on the second sinogram, and, as a difference between the image of the cross section of the first device under test and the image of the cross section of the second device under test, deriving an image representing a difference in the group delay between the first device under test and the second device under test.

10. A computer-readable medium having a program of instructions for execution by a computer to perform a measurement process using an electromagnetic wave measurer having an electromagnetic wave outputter that outputs an electromagnetic wave having a frequency at least equal to 0.01 THz and not more than 100 THz toward a device under test and a container storing at least a part of the device under test; an electromagnetic wave detector that detects the electromagnetic wave which has transmitted through the device under test; and a relative position changer that changes a relative position of an intersection at which an optical path of the electromagnetic wave transmitting through the device under test and the device under test intersect with respect to the device under test, the measurement process comprising:

recording a delay period of the electromagnetic wave caused by a transmission of the electromagnetic wave through the container;

deriving, based on a detected result by the electromagnetic wave detector, a phase in the frequency domain of the electromagnetic wave which has transmitted through the device under test;

deriving a delay-corrected phase obtained by subtracting an integral of the delay period with respect to the frequency from the phase;

deriving a sinogram based on a derived result by the deriving of the delay-corrected phase; and deriving, based on the sinogram, an image of a cross section of the device under test including the intersection.

11. A computer-readable medium having a program of instructions for execution by a computer to perform a measurement process using an electromagnetic wave measurer having an electromagnetic wave outputter that outputs an electromagnetic wave having a frequency at least equal to 0.01 THz and not more than 100 THz toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changer that changes a relative position of a first intersection at which an optical path of the electromagnetic wave transmitting through the first device under test and the first device under test intersect with respect to the first device under test, the measurement process comprising:

recording a delay period of the electromagnetic wave caused by a transmission of the electromagnetic wave through the container;

deriving, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test;

deriving a delay-corrected phase obtained by subtracting an integral of the delay period with respect to the frequency from the first phase;

deriving, based on a derived result by the deriving of the delay-corrected phase and the second phase, a first group delay in the frequency domain of the electromagnetic wave which has transmitted through the first device under test, and a second group delay in the frequency domain of the electromagnetic wave which has transmitted through the second device under test;

deriving, based on a difference between the first group delay and the second group delay, a sinogram for a difference in the group delay between the first device under test and the second device under test; and deriving, based on the sinogram, an image of a cross section of the device under test including the intersection.

12. A computer-readable medium having a program of instructions for execution by a computer to perform a measurement process using an electromagnetic wave measurer having an electromagnetic wave outputter that outputs an electromagnetic wave having a frequency at least equal to 0.01 THz and not more than 100 THz toward a first device under test and a container storing at least a part of the first device under test, and further outputs the electromagnetic wave toward a second device under test; an electromagnetic wave detector that detects the electromagnetic wave which has transmitted through the first device under test and the electromagnetic wave which has transmitted through the second device under test; and a relative position changer that changes a relative position of a first intersection at which an optical path of the electromagnetic wave transmitting through the first device under test and the first device under test intersect with respect to the first device under test, the measurement process comprising:

recording a delay period of the electromagnetic wave caused by a transmission of the electromagnetic wave through the container;

deriving, based on a detected result by the electromagnetic wave detector, a first phase which is a phase in the frequency domain of the electromagnetic wave which has transmitted through the first device under test, and a second phase which is a phase in the frequency domain of the electromagnetic wave which has transmitted through the second device under test;

deriving a delay-corrected phase obtained by subtracting an integral of the delay period with respect to the frequency from the first phase;

deriving, based on a derived result by the deriving of the delay-corrected phase and the second phase, a first group delay in the frequency domain of the electromagnetic wave which has transmitted through the first device under test, and a second group delay in the frequency domain of the electromagnetic wave which has transmitted through the second device under test;

deriving a first sinogram based on the first group delay, and a second sinogram based on the second group delay; and deriving an image of a cross section of the first device under test based on the first sinogram, and an image of a cross section of the second device under test based on the second sinogram, and, as a difference between the image of the cross section of the first device under test and the image of the cross section of the second device under test, deriving an image representing a difference in the group delay between the first device under test and the second device under test.

\* \* \* \* \*